US012611149B2

(12) United States Patent
Kato

(10) Patent No.:  US 12,611,149 B2
(45) Date of Patent:  Apr. 28, 2026

(54) X-RAY IMAGING APPARATUS AND X-RAY IMAGING SYSTEM

(71) Applicant: SHIMADZU CORPORATION, Kyoto (JP)

(72) Inventor: Mikihiko Kato, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 167 days.

(21) Appl. No.: 18/764,655

(22) Filed: Jul. 5, 2024

(65) Prior Publication Data

US 2025/0032082 A1     Jan. 30, 2025

(30) Foreign Application Priority Data

Jul. 26, 2023    (JP) ................................. 2023-121593

(51) Int. Cl.
*A61B 6/04* (2006.01)
*A61B 6/00* (2006.01)
*A61B 6/10* (2006.01)
*A61B 6/46* (2024.01)

(52) U.S. Cl.
CPC .............. *A61B 6/10* (2013.01); *A61B 6/0407* (2013.01); *A61B 6/0421* (2013.01); *A61B 6/0487* (2020.08); *A61B 6/5294* (2013.01); *A61B 6/547* (2013.01); *A61B 6/464* (2013.01); *A61B 6/467* (2013.01)

(58) Field of Classification Search
CPC ......... A61B 6/547; A61B 6/03; A61B 6/0407; A61B 6/5294; A61B 6/545; A61B 6/0487; A61B 6/0421; A61B 6/4411; A61B 6/46; A61B 6/54
See application file for complete search history.

(56) References Cited

U.S. PATENT DOCUMENTS

2009/0306494 A1*  12/2009  Scarth .................. G01R 33/381
                                                              378/63
2019/0298285 A1*  10/2019  Rakic ...................... A61B 6/04

FOREIGN PATENT DOCUMENTS

JP          2017-164131 A       9/2017

* cited by examiner

*Primary Examiner* — Uzma Alam
*Assistant Examiner* — Mamadou Faye
(74) *Attorney, Agent, or Firm* — Muir Patent Law, PLLC

(57) ABSTRACT

The X-ray imaging apparatus is provided with an image processing unit for acquiring the presence or absence of a subject holding member, and a controller. The controller is configured to acquire a movement-prohibited direction which is a direction in which the subject holding member is not provided, based on the presence or absence of the subject holding member, and perform at least one of restricting the operation of the table top moving mechanism and notifying that the direction of tilting the table top and the movement-prohibited direction coincide, when the direction of tilting the table top and the movement prohibited direction coincide.

13 Claims, 9 Drawing Sheets

FIG.2

*FIG. 13*                    Table top operation control processing

Table top movement-prohibition releasing processing

X-RAY IMAGING APPARATUS AND X-RAY IMAGING SYSTEM

CROSS-REFERENCE TO RELATED APPLICATIONS

The related Japanese Patent Application No. 2023-121593, entitled "X-ray Imaging Apparatus and X-ray imaging System," filed on Jul. 26, 2023, invented by KATO Mikihiko, upon which this patent application is based, is herein incorporated by reference.

BACKGROUND OF THE INVENTION

Field of the Invention

The present invention relates to an X-ray imaging apparatus and an X-ray imaging system, more particularly to an X-ray imaging apparatus and an X-ray imaging system equipped with a table top for placing a subject thereon and configured to perform X-ray imaging by changing the tilt of the table top.

Description of the Related Art

The following description sets forth the inventor's knowledge of the related art and problems therein and should not be construed as an admission of knowledge in the prior art.

Conventionally, an X-ray imaging apparatus equipped with a table top for placing a subject thereon and configured to perform imaging while changing the tilt of the table top is known. Such an X-ray imaging apparatus is disclosed, for example, in Japanese Patent Application Publication No. 2017-164131.

In the above-described Japanese Patent Application Publication No. 2017-164131 discloses an X-ray fluoroscopic imaging apparatus equipped with a fluoroscopic imaging table, an X-ray tube device, an X-ray detector, and a controller. The fluoroscopic imaging table disclosed in the above-described Japanese Patent Application Publication No. 2017-164131 is equipped with a table top for placing a subject thereon, a rolling mechanism for rotating the table top, and a grip bar for the subject to grip during the rotation of the table top.

Further, the controller disclosed in the above-described Japanese Patent Application Publication No. 2017-164131 is configured to estimate the position of the center of gravity of the subject placed on the table top and to control the operation of the table top based on the estimated position of the center of gravity. Specifically, the controller disclosed in the above-described Japanese Patent Application Publication No. 2017-164131 is configured to decelerate the rotation speed of the table top when the center of gravity of the subject is higher than the center of rotation of the table top and the subject is not gripping the grip bar.

Further, the controller disclosed in the above-described Japanese Patent Application Publication No. 2017-164131 is configured not to decelerate the rotation speed of the table top when the center of gravity of the subject is lower than the center of rotation of the table top or when the subject is gripping the grip portion.

Here, the configuration disclosed in the above-described Japanese Patent Application Publication No. 2017-164131 is configured to suppress (restrict) the rotation (movement) of the table top only when the center of gravity of the subject is high and the subject is not gripping the grip bar (subject holding member). However, although not disclosed in the above-described Japanese Patent Application Publication No. 2017-164131, in the X-ray imaging apparatuses that performs imaging while rotating (tilting) the table top, there are cases in which the table top is tilted in a direction in which the subject holding member is not provided.

In the configuration disclosed in the above-described Japanese Patent Application Publication No. 2017-164131, when the subject holding member is not provided, it is determined that the subject holding member is not gripped. Only when it is determined that the subject holding member is not gripped and the center of gravity of the subject is high, the movement of the table top is restricted. Further, when the center of gravity of the subject is low, or when it is determined that the subject holding member is being gripped by the subject, the operation of the table top is not restricted.

However, for example, in the case where the table top is tilted toward the right-hand side of the subject in a state in which the subject is gripping the subject holding member positioned near the subject's waist with his or her right hand, even if the subject is gripping the subject holding member, the table top may not be able to support the subject's weight properly, and the subject's position on the table top may shift. In other words, regardless of whether the subject is gripping the subject holding member, there is an inconvenience that the position of the subject on the table top may shift depending on the direction in which the table top is tilted.

However, the above-described Japanese Patent Application Publication No. 2017-164131 does not disclose a configuration that restricts the operation of the table top based on the direction in which the table top is tilted. Therefore, in the configuration disclosed in the above-described Japanese Patent Application Publication No. 2017-164131, there is a problem that it is difficult to prevent the shifting of the subject's position on the table top due to the tilting of table top in a predetermined direction.

SUMMARY OF THE INVENTION

One purpose of the present invention is to provide an X-ray imaging apparatus and an X-ray imaging system that can suppress the shifting of the subject's imaging position on the table top due to the tilting of the table top in a predetermined direction.

An X-ray imaging apparatus according to one aspect of the present invention includes:

an X-ray irradiation unit configured to emit X-rays;

an X-ray detector configured to detect X-rays emitted from the X-ray irradiation unit;

a table top configured to place a subject thereon;

a table top driving mechanism configured to change a tilt of the table top;

an imaging unit configured to image the subject placed on the table top and a subject holding member provided on the table top to hold a posture of the subject;

an image processing unit configured to acquire presence or absence of the subject holding member, based on an image of the subject and the subject holding member captured by the imaging unit; and a controller, wherein the controller is configured to acquire a movement-prohibited direction which is a direction in which the subject holding member is not provided, based on the presence or absence of the subject holding member acquired by the image acquisition acquisition processing unit, determine whether a direction of tilting the table top by the table top driving mechanism and the movement-prohibited direction coincide, and perform, when the direction of tilting the table top and the movement-prohibited direction coincide, at least one of restricting an operation of the table top driving mechanism and notifying that the direction of tilting the table top and the movement-prohibited direction coincide.

An X-ray imaging system according to a second aspect of the present invention includes:

an X-ray irradiation unit configured to emit X-rays;

an X-ray detector configured to detect X-rays emitted from the X-ray irradiation unit;

a table top configured to place the subject thereon;

a table top driving mechanism configured to change a tilt of the table top;

an imaging unit configured to image a subject placed on the table top and a subject holding member provided on the table top to hold a posture of the subject;

an image processing unit configured to acquire presence or absence of the subject holding member, based on an image of the subject and the subject holding member captured by the imaging unit; and a controller, wherein the controller is configured to acquire a movement-prohibited direction which is a direction in which the subject holding member is not provided, based on the presence or absence of the subject holding member acquired by the image acquisition acquisition processing unit, determine whether a direction of tilting the table top by the table top driving mechanism and the movement-prohibited direction coincide, and perform, when the direction of tilting the table top and the movement-prohibited direction coincide, at least one of restricting an operation of the table top driving mechanism and notifying that the direction of tilting the table top and the movement-prohibited direction coincide.

The X-ray imaging apparatus according to the first aspect of the present invention and the X-ray imaging system according to the second aspect of the present invention are provided with an image processing unit for acquiring the presence or absence of a subject holding member based on the image of the subject and the subject holding member, and a controller. The controller is configured to acquire a movement-prohibited direction which is a direction in which the subject holding member is not provided, based on the presence or absence of the subject holding member, determine whether the direction of tilting the table top by the table top driving mechanism and the movement-prohibited direction coincide, and perform at least one of restricting the operation of the table top moving mechanism and notifying that the direction of tilting the table top and the movement-prohibited direction coincide, when the direction of tilting the table top and the movement prohibited direction coincide.

With this configuration, when an operation input to tilt the table top in the direction that coincides with the movement-prohibited direction is received, the operation of the table top driving mechanism is restricted, or it is notified that the direction of tilting the table top and the movement-prohibited direction coincide. In the case where the movement of the table top driving mechanism is restricted, it is possible to prevent the table top from tilting to an angle at which the subject's position on the table top shifts. In addition, in the case where it is notified that the direction of tilting the table top and the movement-prohibited direction coincide, it becomes possible to make the operator aware of the possibility that the subject's position on the table top may shift. This can prompt the operator to stop the movement of the table top driving mechanism. As a result, it is possible to suppress the shifting of the subject's position on the table top due to the tilting of the table top in a predetermined direction.

The foregoing and other objects, features, aspects and advantages of the present invention will become more apparent from the following detailed description of the present invention when taken in conjunction with the accompanying drawings.

BRIEF DESCRIPTION OF THE DRAWINGS

The preferred embodiments of the present disclosure are shown by way of example, and not limitation, in the accompanying figures.

FIG. 2 is a schematic diagram showing a configuration of an X-ray imaging apparatus according to one embodiment.

DETAILED DESCRIPTION OF THE PREFERRED EMBODIMENTS

In the following paragraphs, some preferred embodiments of the present disclosure will be described by way of example and not limitation. It should be understood based on this disclosure that various other modifications can be made by those in the art based on these illustrated embodiments.

Hereinafter, some embodiments in which the present invention is embodied will be described based on the attached drawings.

First, referring to FIG. 1 to FIG. 12, the configuration of an X-ray imaging system 100 equipped with an X-ray imaging apparatus 1 according to one embodiment will be described. The X-ray imaging apparatus 1 is a system for imaging a subject 90 (see FIG. 5) to confirm the branching point of the blood vessel into which the catheter is to be inserted when a doctor performs catheter treatment of the subject 90. In other words, the X-ray imaging apparatus 1 is a so-called fluoroscopic imaging apparatus.

Figure 1:
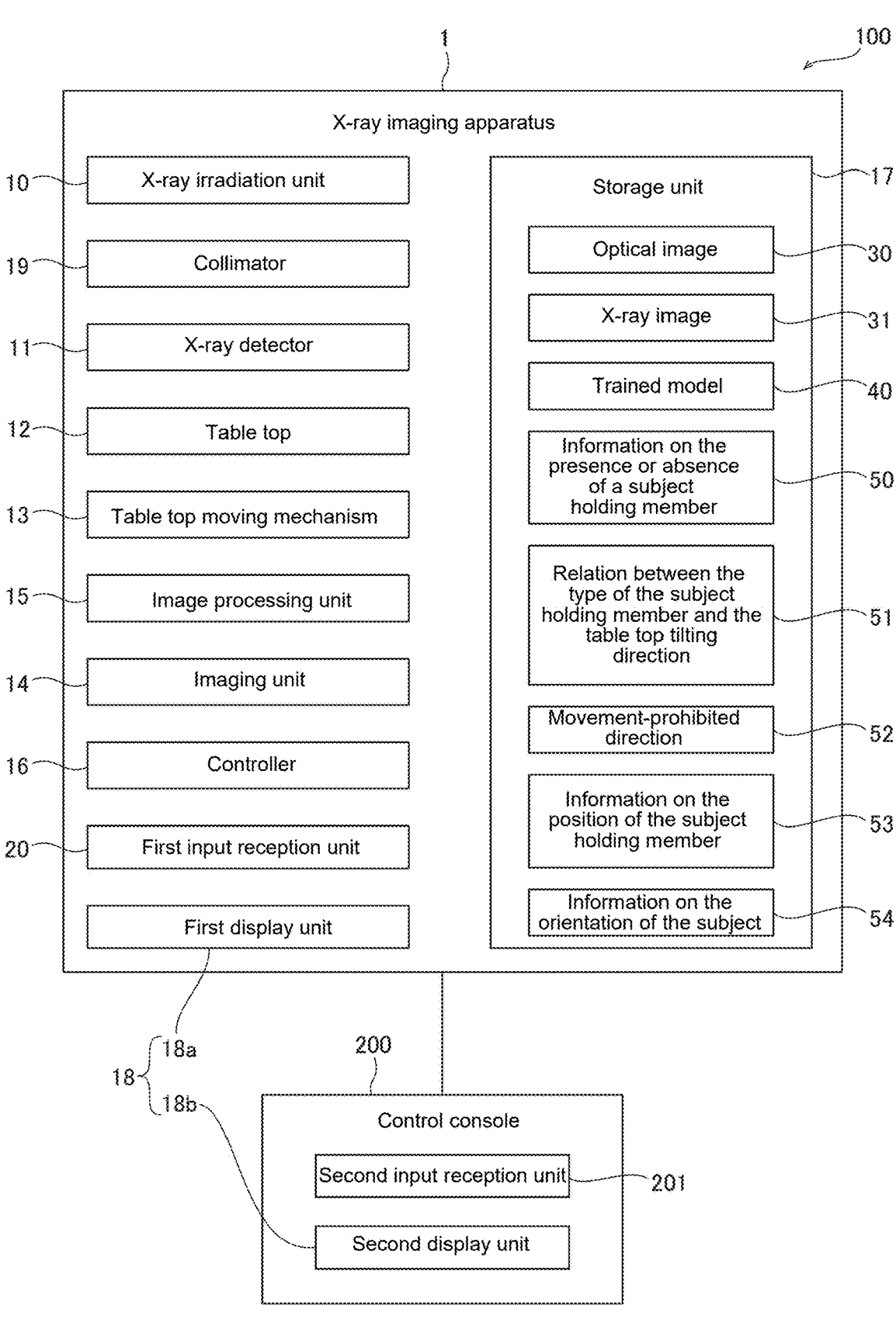
FIG. 1 is a block diagram showing a configuration of an X-ray imaging system equipped with an X-ray imaging apparatus according to one embodiment.

As shown in FIG. 1, the X-ray imaging system 100 is equipped with an X-ray imaging apparatus 1 and a control console 200.

The X-ray imaging apparatus 1 is placed in an operating room, for example. Further, the control console 200 is placed in a room different from the operating room in which the X-ray imaging apparatus 1 is arranged.

As shown in FIG. 1, the X-ray imaging apparatus 1 is equipped with an X-ray irradiation unit 10, an X-ray detector 11, a table top 12, a table top driving mechanism 13, an imaging unit 14, an image processing unit 15, and a controller 16. In this embodiment, the X-ray imaging apparatus 1 is equipped with a storage unit 17 and a display unit 18. Further, the X-ray imaging apparatus 1 is equipped with a collimator 19 and a first input reception unit 20.

The X-ray irradiation unit 10 is configured to irradiate X-rays. The X-ray irradiation unit 10 includes an X-ray generating device, such as an X-ray tube, which generates X-rays when a high-voltage is applied.

The collimator 19 is formed in a flat plate shape and is provided with an opening in the center. The collimator 19 is constructed by forming an opening in a flat plate of, for example, a lead material. The collimator 19 adjusts the irradiation range of X-rays emitted by the X-ray irradiation unit 10 by adjusting the size and shape of the opening under the control of the controller 16.

The X-ray detector 11 is configured to detect X-rays emitted from the X-ray irradiation unit 10. The X-ray detector 11 is, for example, an FPD (Flat Panel Detector), which detects X-rays transmitted through the subject 90.

The table top 12 is configured to support a subject 90 thereon. Further, the table top 12 is driven by the table top driving mechanism 13 to change the tilt. The detailed configuration of the table top 12 will be described below.

The table top driving mechanism 13 is configured to change the tilt of the table top 12. The detailed configuration of the table top driving mechanism 13 will be described later.

The imaging unit 14 is configured to image the subject 90 placed on the table top 12 and the subject holding member 21 (see FIG. 2), which is arranged on the table top 12 to hold the posture of the subject 90. In this embodiment, the imaging unit 14 is configured to capture an optical image 30. The imaging unit 14 is, for example, an optical camera. The optical camera is an imaging device that includes an image sensor capable of receiving visible light, such as, e.g., a CMOS (Complementary Metal Oxide Semiconductor) sensor and a CCD (Charge Coupled Device) sensor.

The image processing unit 15 is configured to generate the X-ray image 31 based on the X-rays detected by the X-ray detector 11. Further, in this embodiment, the image processing unit 15 is configured to acquire the presence or absence of the subject holding member 21 based on the image (the optical image 30) of the subject 90 and the subject holding member 21, which were captured by the imaging unit 14. Specifically, the image processing unit 15 is configured to acquire information on whether the subject holding member 21 is arranged on the table top 12, as information 50 on the presence or absence of the subject holding member 21. Further, in this embodiment, the image processing unit 15 is configured to acquire information 53 on the position of the subject holding member 21 and information 54 on the orientation of the subject 90. The image processing unit 15 is configured by a processor, such as a CPU (Central Processing Unit), a GPU (Graphics Processing Unit), an FPGA (Field-Programmable Gate Array) configured for image processing, or a circuit (Circuitry), and a memory, such as a ROM (Read Only Memory) and a RAM (Random Access Memory). Regarding the configuration for the image processing unit 15 to acquire the information 50 on the presence or absence of the subject holding member 21, the information 53 on the position of the subject holding member 21, and the information 54 on the position of the subject 90, the details will be described later.

The controller 16 is configured to control the entire X-ray imaging apparatus 1. Specifically, the controller 16 is configured to perform control of X-ray irradiation by the X-ray irradiation unit 10, such as start and stop of X-ray irradiation, control of changing the X-ray irradiation range by the collimator 19, control of the detection by the X-ray detector 11, and so on. Further, the controller 16 is configured to control the table top driving mechanism 13 to change the tilt of the table top 12. The controller 16 is composed of a processor, such as a CPU and a circuitry, and a memory, such as a ROM and a RAM.

The storage unit 17 is configured to store various programs to be executed by the controller 16. Further, the storage unit 17 is configured to store the optical images 30 captured by the imaging unit 14. Further, the storage unit 17 is configured to store the X-ray image 31 generated by the image processing unit 15. Further, the storage unit 17 is configured to store the trained model 40 which will be described later. Further, the storage unit 17 is configured to store the information 50 on the presence or absence of the subject holding member 21, the information 53 on the position of the subject holding member 21, and the information 54 on the orientation of the subject 90, all of which are acquired by the image processing unit 15. Further, the storage unit 17 is configured to store the relation 51 between the type of the subject holding member 21 and the direction of tilting the table top 12. Further, the storage unit 17 is configured to store the movement-prohibited direction 52 acquired by the controller 16. The storage unit 17 includes a non-volatile storage device, such as an HDD (Hard Disk Drive) and an SSD (Solid State Drive).

The display unit 18 is configured to display the X-ray image 31. The display unit 18 is a display device, such as a liquid crystal display monitor or an organic EL (Electro Luminescence) monitor. In this embodiment, the display unit 18 includes a first display unit 18a, which is owned by the X-ray imaging apparatus 1, and a second display unit 18b, which is owned by the control console 200.

The first input reception unit 20 is configured to receive an operation input from the operator. Specifically, the first input reception unit 20 is configured to accept an operation input to change the tilt of the table top 12. The first input reception unit 20 includes, for example, a push button, an operation lever, and so on.

Further, as shown in FIG. 1, the control console 200 has a second input reception unit 201 and a second display unit 18b.

The second input reception unit 201 is configured to receive an operation input from the operator. Specifically, the second input reception unit 201 is configured to receive an operation input to change the tilt of the table top 12. The second input reception unit 201 includes, for example, a push button, an operation lever 201a (see FIG. 4) and so on. (Configurations of X-Ray Imaging Apparatus and Table Top Moving Mechanism)

Figure 2:
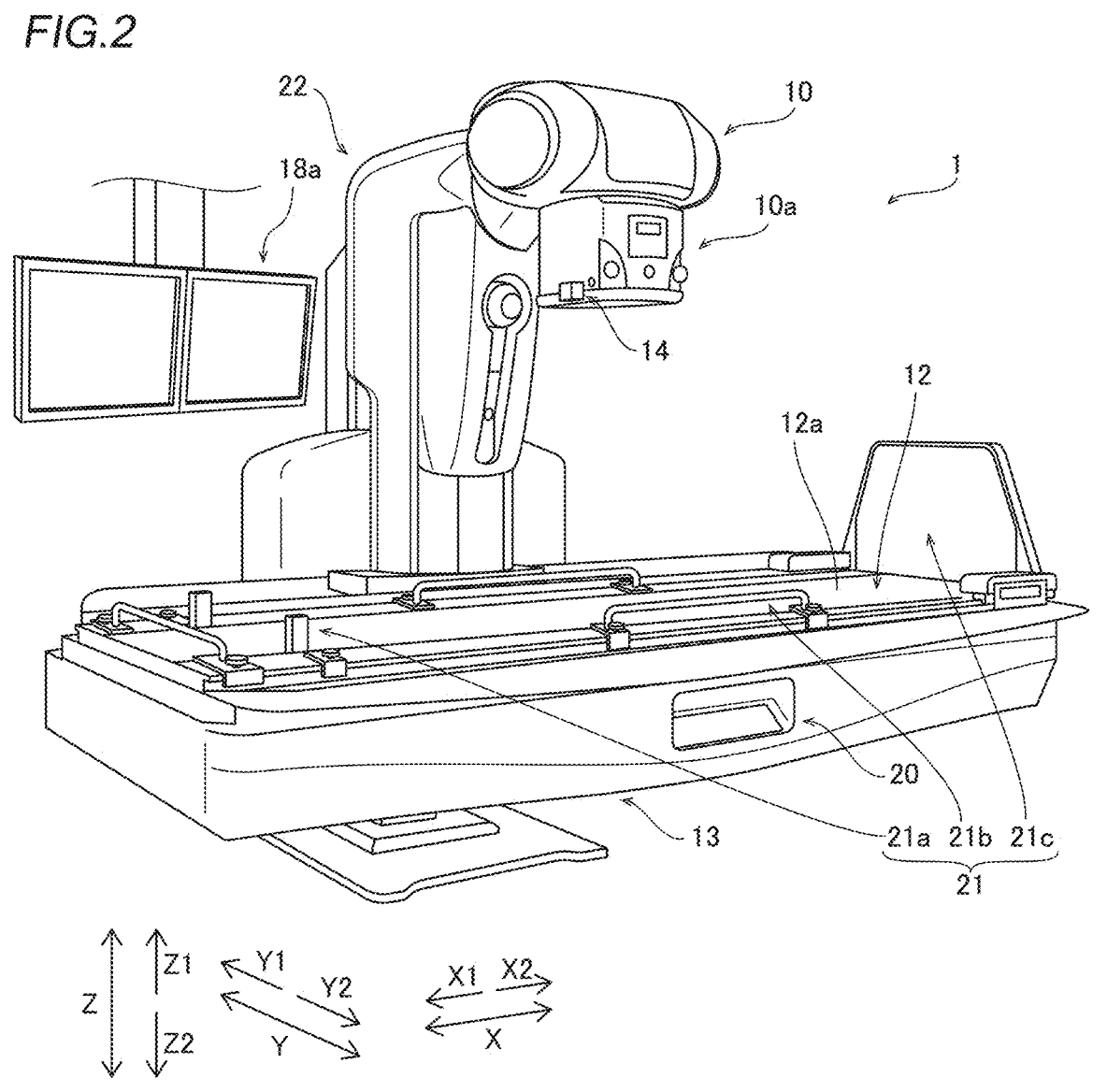

As shown in FIG. 2, in the X-ray imaging apparatus 1, the X-ray irradiation unit 10 is movably supported by the X-ray irradiation unit moving mechanism 22. The X-ray irradiation unit moving mechanism 22 is equipped with a motor and electromagnetic brake, which are not illustrated, corresponding to each of the X-direction, the Y-direction, and the Z-direction. And, the X-ray irradiation unit 10 is configured to be movable in each of the X-direction, the Y-direction, and the Z-direction by the operator.

Note that in the example shown in FIG. 2, the vertical direction is referred to as a Z-direction, the upward direction as a Z1-direction, and the downward direction as a Z2-direction. Further, of the two directions orthogonal to the Z-direction, one of them is referred to as an X-direction, and the other the Y-direction. Further, of the X-direction, a direction toward one side is referred to as an X1-direction, and a direction toward the other side as an X2-direction. Further, of the Y-direction, a direction toward one side is referred to as an Y1-direction, and a direction toward the other side as an Y2-direction. In the example shown in FIG. 2, it is illustrated such that the longitudinal direction of the table top 12 is along the X-direction.

Further, the X-ray irradiation unit 10 is configured to be rotatable about the Y-axis in a state of being held by the X-ray irradiation unit moving mechanism 22. Therefore, the X-ray irradiation unit 10 is configured to be capable of changing the direction and angle of the X-ray irradiation. Further, the X-ray irradiation unit moving mechanism 22 is equipped with a motor and an electromagnetic brake, which are not illustrated, corresponding to the axis (Y-axis) of the X-ray irradiation unit 10 which is not illustrated. The X-ray irradiation unit moving mechanism 22 according to this embodiment moves the X-ray irradiation unit 10 in the direction corresponding to the direction of the operation force input by the operator when the operator moves the X-ray irradiation unit 10.

Further, as shown in FIG. 2, the X-ray imaging apparatus 1 is equipped with one imaging unit 14. In this configuration, the imaging unit 14 is arranged in the housing 10a of the X-ray irradiation unit 10. Specifically, the imaging unit 14 is provided at a position facing the table top 12 in the housing 10a of the X-ray irradiation unit 10.

Further, the table top 12 has a placement surface 12a on which the subject 90 (see FIG. 5) is placed. Further, the table top 12 is configured to be movable in each of the X-direction, the Y-direction, and the Z-direction by the table top driving mechanism 13. Further, the table top 12 is configured to be rotatable in the rotation direction about the X axis by the table top driving mechanism 13. Further, the table top 12 is configured to be rotatable in the rotation direction about the Y-axis by the table top driving mechanism 13.

Further, the table top driving mechanism 13 is configured to move the table top 12 in each of the X-direction, the Y-direction, and the Z-direction. The table top driving mechanism 13 is equipped with a motor and electromagnetic brake, which are not illustrated, corresponding to each of the X-direction, the Y-direction, and the Z-direction. Further, the table top driving mechanism 13 is configured to rotate the table top 12 about the X-axis. Further, the table top driving mechanism 13 is configured to rotate the table top 12 in the rotation direction about the Y-direction axis. The table top driving mechanism 13 is equipped with a motor for rotating the table top 12 and an electromagnetic brake corresponding to each of the two axes (X-axis and Y-axis) about which the table top 12 can be rotated. The table top driving mechanism 13 according to this embodiment moves the table top 12 and changes the tilt of the table top 12 in a direction corresponding to the direction of the operation force input by the operator via the first input reception unit 20 or the second input reception unit 201 (see FIG. 1) when the operator moves the table top 12.

Further, as shown in FIG. 2, the first display unit 18a is arranged at a position in an operating room where an operator such as a doctor can confirm the X-ray image 31 (see FIG. 1). The first display unit 18a is held, for example, by a suspension device (not illustrated) mounted on the ceiling of the operating room. Note that the first display unit 18a may be configured to be movable and held by a device holding the display unit.

As shown in FIG. 2, the subject holding member 21 includes at least one of a shoulder rest 21a, a grip bar 21b, and a stepping platform 21c. In the example shown in FIG. 2, the subject holding member 21 includes all of the shoulder rest 21a, the grip bar 21b, and the stepping platform 21c.

The shoulder rest 21a is configured to support the posture of the subject 90 when the table top 12 is tilted reversely (tilting the table top 12 in the direction of lowering the head 90a (see FIG. 5) of the subject 90 (see FIG. 5) and raising the foot 90b (see FIG. 5)). In this embodiment, the shoulder rest 21a is configured to be manually attachable to and detachable from the table top 12 by the operator. Further, the shoulder rest 21a is configured so that its position on the table top 12 can be manually changed by the operator.

Further, the grip bar 21b is provided for the subject 90 to grip when the table top 12 is tilted. The grip bar 21b can support the posture of the subject 90 by being griped by the subject 90. In this embodiment, the grip bar 21b is configured to be manually attachable to and detachable from the table top 12 by the operator. Further, the grip bar 21b is configured so that its position on the table top 12 can be manually changed by the operator.

The stepping platform 21c is configured to support the posture of the subject 90 when the table top 12 is tilted (tilting the table top 12 in the direction of raising the head 90a and lowering the foot 90b). In this embodiment, the stepping platform 21c is configured to be manually attachable to and detachable from the table top 12 by the operator. Further, the stepping platform 21c is configured to be manually changeable in the position on the table top 12 by the operator.
(Control Console)

Figure 3:
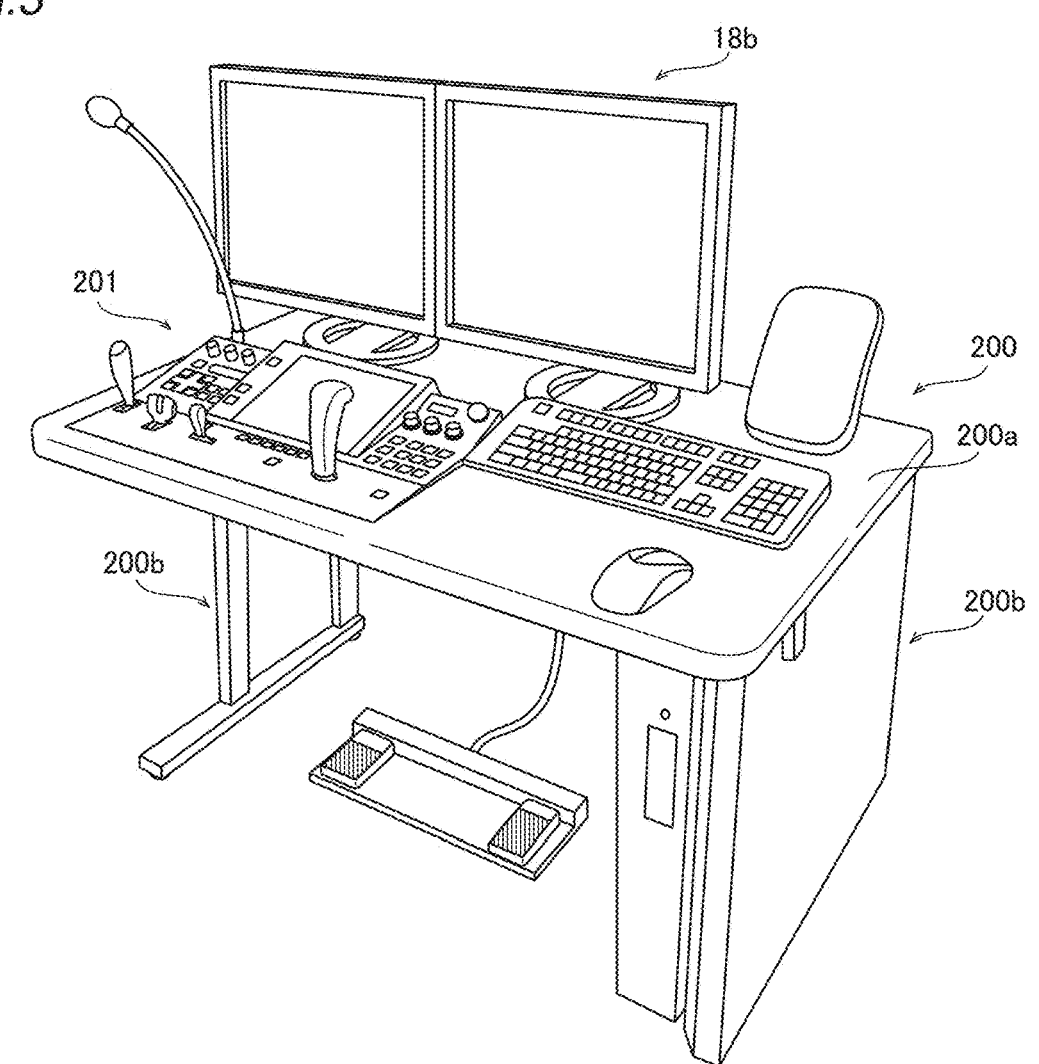
FIG. 3 is a schematic diagram showing a configuration of a control console equipped in an X-ray imaging system according to one embodiment.

FIG. 3 is a schematic diagram of the control console 200 as viewed from an oblique direction. As shown in FIG. 3, the control console 200 has a placement surface 200a on which the second input reception unit 201 and the second display unit 18*b* are placed, and a support member 200*b* that supports the placement surface 200*a*.

As shown in FIG. 3, the second input reception unit 201 is arranged on the placement surface 200*a* of the control console 200. Further, the second display unit 18*b* is arranged on the placement surface 200*a* of the control console 200.

(Second Input Reception Unit)

Figure 4:
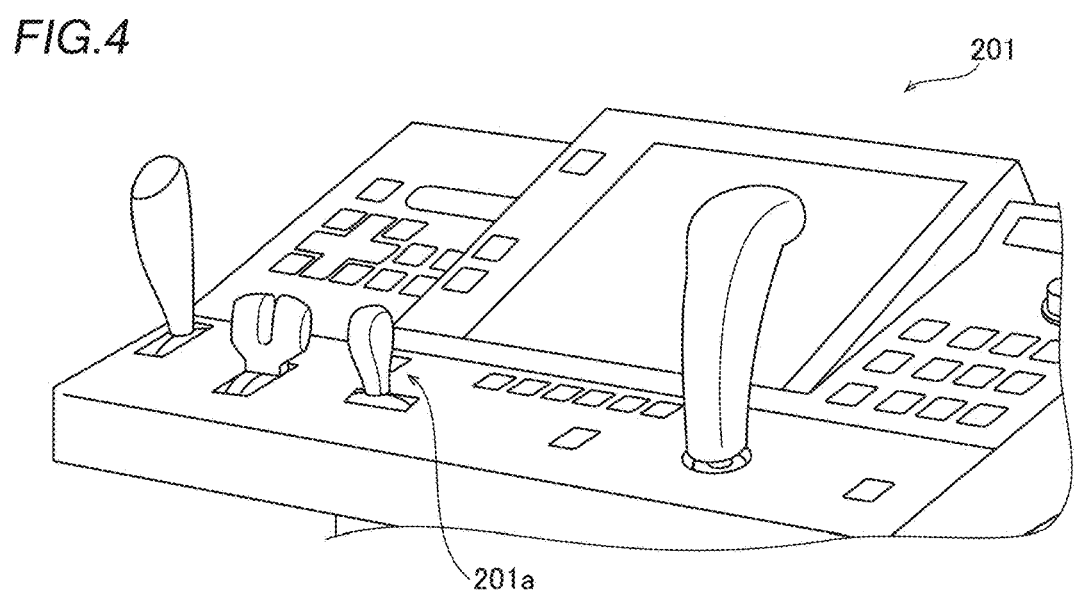
FIG. 4 is an enlarged schematic diagram of a second input reception unit in a control console according to one embodiment.

FIG. 4 is an enlarged view of the control console 200 (see FIG. 3), showing the vicinity of the second input reception unit 201. As shown in FIG. 4, the second input reception unit 201 includes an operation lever 201*a*.

The operation lever 201*a* is configured to receive an operation input for changing the tilt of the table top 12 (see FIG. 2). The controller 16 (see FIG. 1) is configured to change the tilt of the table top 12 based on the operation input received by the operation lever 201*a*. In other words, the controller 16 performs control to tilt the table top 12 in a direction corresponding to the direction in which the operation lever 201*a* is tilted.

(Optical Image)

Figure 5:
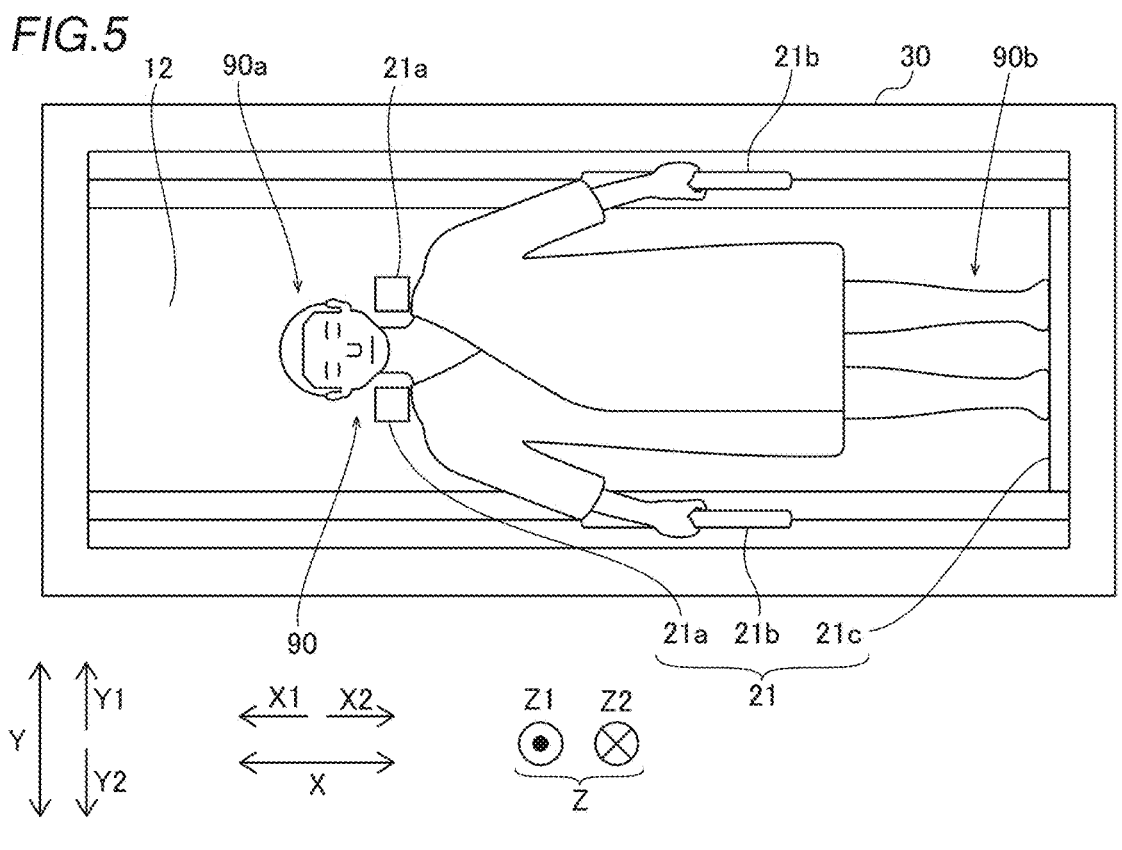
FIG. 5 is a schematic diagram for explaining an image captured by an imaging unit according to one embodiment.

The optical image 30 shown in FIG. 5 is an image captured by the imaging unit 14 (see FIG. 1). In the example shown in FIG. 5, the table top 12, the subject 90, and the subject holding member 21 are shown in the optical image 30. Specifically, the optical image 30 shows the subject 90, a pair of shoulder rests 21*a*, a pair of grip bars 21*b*, and a stepping platform 21*c*.

Here, when tilting the table top 12, the subject 90 may fall off the table top 12 if the subject holding member 21 is not provided at a location corresponding to the tilting direction. For example, if the stepping platform 21*c* is not provided when the table top 12 is tilted, if the shoulder rest 21*a* is not provided when the table top 12 is tilted reversely, or if the grip bar 21*b* is not provided when the table top 12 is rotated about the X-axis, the subject 90 may fall off from the table top 12.

Therefore, in this embodiment, the controller 16 (see FIG. 1) is configured to restrict the operation of the table top driving mechanism 13 (see FIG. 2) when there is a possibility that the position of the subject 90 on the table top 12 may shift due to the tilting of the table top 12, or to notify that the position of the subject 90 on the table top 12 may shift due to the tilting of the table top 12.

Specifically, the controller 16 is configured to acquire the movement-prohibited direction 52 (see FIG. 1), which is the direction in which the subject holding member 21 is not provided, based on the presence or absence of the subject holding member 21 acquired by the image processing unit 15 (see FIG. 1). Further, the controller 16 is configured to determine whether the direction of tilting the table top 12 by the table top driving mechanism 13 and the movement-prohibited direction 52 coincide. Further, the controller 16 is configured to perform at least one of the restriction on the movement of the table top driving mechanism 13 and the notification that the direction of tilting the table top 12 and the movement-prohibited direction 52 coincide, when the direction of tilting the table top 12 and the movement-prohibited direction 52 coincide.

(Acquisition of Presence or Absence and Position of Subject Holding Member, and Orientation of Subject)

Figure 6:
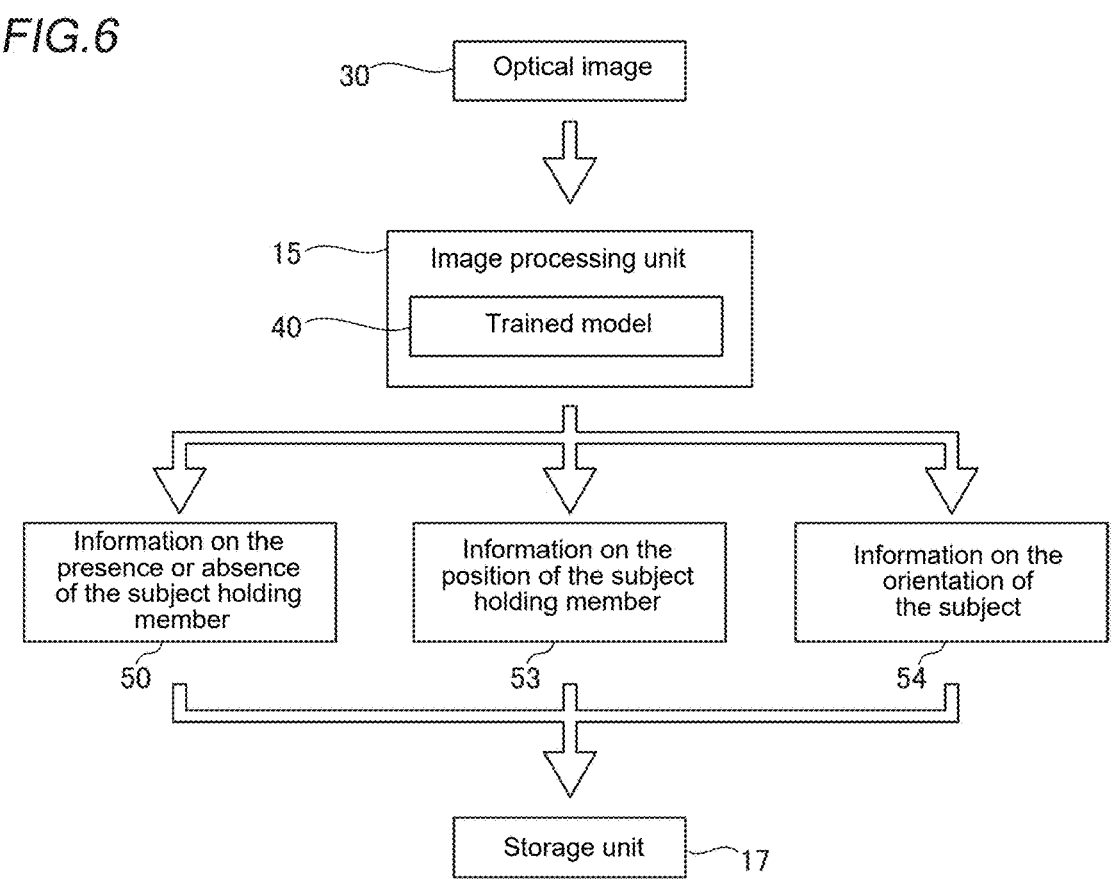
FIG. 6 is a schematic diagram for explaining a configuration in which an image processing unit according to one embodiment acquires information on the presence or absence of a subject holding member, information on the position of the subject holding member, and information on the orientation of the subject.

Referring to FIG. 6, the configuration of acquiring the presence or absence of the subject holding member 21 (see FIG. 5) by the image processing unit 15 will be described. In this embodiment, as shown in FIG. 6, the image processing unit 15 acquires the presence or absence of the subject holding member 21 based on the captured optical image 30 of the subject 90 (see FIG. 5) and the subject holding member 21 captured by the imaging unit 14 (see FIG. 1). Specifically, the image processing unit 15 is configured to acquire the presence or absence of the subject holding member 21 by acquiring whether at least one of the shoulder rest 21*a* (see FIG. 5), the grip bar 21*b* (see FIG. 5), and the stepping platform 21*c* (see FIG. 5) is provided on the table top 12.

In this embodiment, the image processing unit 15 is configured to acquire information 50 on the presence or absence of the subject holding member 21 based on the presence or absence of the subject holding member 21. For example, the image processing unit 15 acquires information on whether the shoulder rest 21*a* is provided, information on whether the grip bar 21*b* is provided, and information on whether the stepping platform 21*c* is provided, as well as information 50 on whether the subject holding member 21 is provided.

Further, in this embodiment, the image processing unit 15 is configured to acquire the presence or absence of the subject holding member 21, as well as the orientation of the subject 90 on the table top 12, and the position of the subject holding member 21, based on the optical image 30 of the subject 90 and the subject holding member 21 captured by the imaging unit 14.

In this embodiment, the image processing unit 15 is configured to acquire the information 53 on the position of the subject holding member 21 and the information 54 on the orientation of the subject 90. For example, the image processing unit 15 acquires information on which direction side in the X-direction the head 90*a* of the subject 90 (see FIG. 5) is positioned, as the information 53 on the orientation of the subject 90. Further, the image processing unit 15 is configured to acquire the position coordinates of the position where the subject holding member 21 appears in the optical image 30 as the position information 53 of the subject holding member 21.

Further, in this embodiment, the image processing unit 15 is configured to acquire the position of the subject holding member 21 by the trained model 40 that has been trained to acquire the position of the subject holding member 21 on the table top 12 (see FIG. 5). Further, the image processing unit 15 is configured to acquire the orientation of the subject 90 by the trained model 40. In other words, the trained model 40 is generated by learning to acquire the position of the subject holding member 21 and the orientation of the subject 90.

Note that the X-ray irradiation unit 10 may irradiate X-rays in a state directly facing the table top 12 and in a state tilted to the table top 12. Therefore, when generating the trained model 40, it is preferable to generate the trained model 40 using an image captured from a position directly facing the table top 12 and an image captured from an oblique direction to the table top 12.

In this embodiment, the image processing unit 15 is configured to store in the storage unit 17 the acquired information 50 on the presence or absence of the subject holding member 21, the information 53 on the position of the subject holding member 21, and the information 54 on the orientation of the subject 90.

(Acquisition of Movement-Prohibited Direction)

Next, referring to FIG. 7 to FIG. 11, the configuration for the controller 16 (see FIG. 7) to acquire the movement-prohibited direction 52 (see FIG. 7) will be described.

The controller 16 determines whether the subject holding member 21 (see FIG. 5) corresponding to one of the shoulder rest 21*a* (see FIG. 5), the grip bar 21*b* (see FIG. 5), and the stepping platform 21*c* (see FIG. 5) is arranged at the position corresponding to the direction of tilting the table top 12 (see FIG. 5). The controller 16 is configured to set the direction in which the subject holding member 21 corresponding to the shoulder rest 21*a*, the grip bar 21*b*, and the stepping platform 21*c* is not provided at the position corresponding to the direction of tilting the table top 12 as the movement-prohibited direction 52.

Note that even in the case where the subject holding member 21 is provided on the table top 12, depending on the orientation of the subject 90 and the position of the subject holding member 21, the position of the subject 90 on the table top 12 may shift due to the tilting of the table top 12. For example, in the case where the stepping platform 21*c* is placed on the side of the head 90*a* of the subject 90 (see FIG. 8) and the grip bar 21*b* is placed at a position where the subject 90 cannot grip it, when the table top 12 is tilted so that the head 90*a* of the subject 90 is raised, the position of the subject 90 on the table top 12 may shift. Therefore, in this embodiment, the controller 16 is configured to set the movement-prohibited direction 52 based on the orientation of the subject 90 on the table top 12 and the presence or absence and the position of the subject holding member 21.

In this embodiment, the controller 16 sets the movement-prohibited direction 52 based on the information 50 on the presence or absence of the subject holding member 21, the information 53 on the position of the subject holding member 21, and the information 54 on the orientation of the subject 90 stored in the storage unit 17. Further, the controller 16 is configured to store the set movement-prohibited direction 52 in the storage unit 17.

Figure 8:
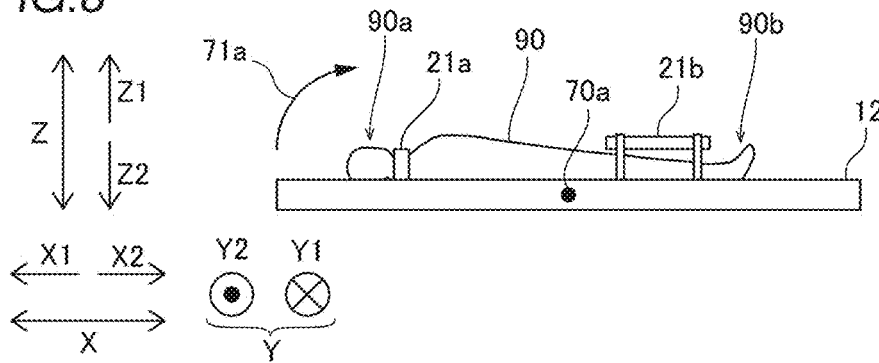
FIG. 8 is a schematic diagram for explaining a configuration in which a controller according to one embodiment sets the tilting direction to a movement-prohibited direction.

FIG. 8 is a schematic diagram of the table top 12 on which the subject 90 is placed, as viewed from the Y2-direction side. As shown in FIG. 8, the shoulder rest 21*a* is provided on the table top 12 near the head 90*a* of the subject 90. Further, as shown in FIG. 8, the grip bar 21*b* is provided on the table top 12 near the foot 90*b* of the subject 90. In other words, the grip bar 21*b* is arranged at a position where the subject 90 cannot grip. Further, in the example shown in FIG. 8, the stepping platform 21C (see FIG. 5) is not provided. As shown in FIG. 8, in the case where the stepping platform 21*c* is not provided at a position where the subject 90 can be supported and the grip bar 21*b* is not located at a position where the subject 90 can be gripped, when the table top 12 is tilted in the tilting direction (in the rotation direction shown by the arrow 71*a* centered on the rotation center 70*a*), the position of the subject 90 on the table top 12 may shift due to the tilting of the table top 12. Therefore, the controller 16 sets the tilting direction as the movement-prohibited direction 52 in a case where the stepping platform 21*c* is not provided at a position where the subject 90 can be supported and the grip bar 21*b* is not located at a position where the subject 90 can grip.

Figure 9:
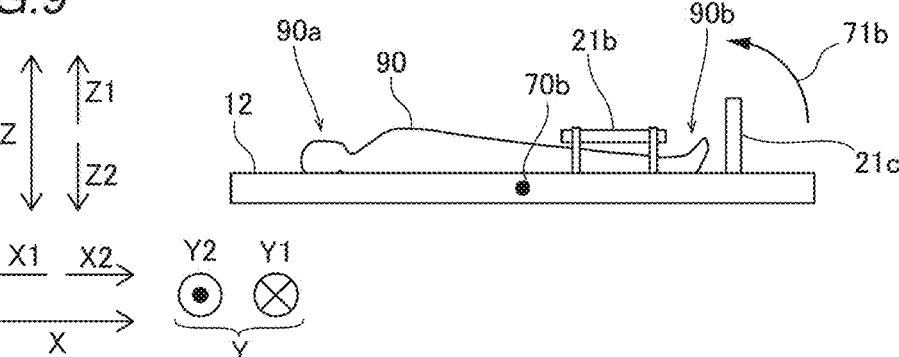
FIG. 9 is a schematic diagram for explaining a configuration in which a controller according to one embodiment sets the reverse tilting direction to a movement-prohibited direction.

FIG. 9 is a schematic diagram of the table top 12 on which the subject 90 is placed, as viewed from the Y2-direction side. Further, as shown in FIG. 9, the stepping platform 21*c* is provided on the table top 12 near the foot 90*b* of the subject 90. Further, as shown in FIG. 9, the grip bar 21*b* is provided on the table top 12 near the foot 90*b* of the subject 90. In other words, the grip bar 21*b* is arranged at a position where the subject 90 cannot grip.

Further, in the example shown in FIG. 9, the shoulder rest 21*a* (see FIG. 8) is not provided near the head 90*a* of the subject 90. As shown in FIG. 9, in the case where the shoulder rest 21*a* is not provided at a position where the subject 90 can be supported and the grip bar 21*b* is not located at a position where the subject 90 can grip, when the table top 12 is tilted in a reverse direction (in the rotation direction shown by the arrow 71*b* centered on the rotation center 70*b*), the position of the subject 90 on the table top 12 may shift due to the tilting of the table top 12. Therefore, the controller 16 sets the reverse direction of the table top 12 as the movement-prohibited direction 52 in a case where the shoulder rest 21*a* is not provided at a position where the subject 90 can be supported and the grip bar 21*b* is not located at a position where the subject 90 can grip.

Figure 10:
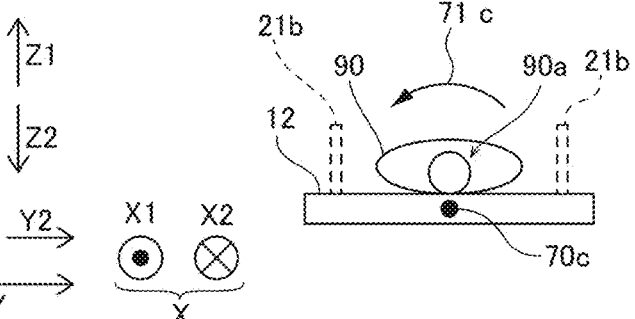
FIG. 10 is a schematic diagram for explaining a configuration in which the controller according to one embodiment sets one of the rotation directions with the head-foot direction as an axis to the movement-prohibited direction.

FIG. 10 is a schematic diagram of the table top 12 on which the subject 90 is placed, as viewed from the X1-direction side. As shown in FIG. 10, the table top 12 has no shoulder rest 21*a* (see FIG. 8) or stepping platform 21*c* (see FIG. 9). Further, in the example shown in FIG. 10, the grip bar 21*b* is positioned on the table top 12 near the foot 90*b* of the subject 90 (see FIG. 9). In other words, the grip bar 21*b* is arranged at a position where the subject 90 cannot grip.

Note that in FIG. 10, the grip bar 21*b* is shown with a dashed line to indicate that the subject 90 is unable to grip it. As shown in FIG. 10, in the case where the grip bar 21*b* is not located at a position where the subject 90 can grip, when the table top 12 is tilted in the direction indicated by the arrow 71*c* centered on the rotation center 70*c*, the position of the subject 90 on the table top 12 may shift due to the tilting of the table top 12.

Figure 11:
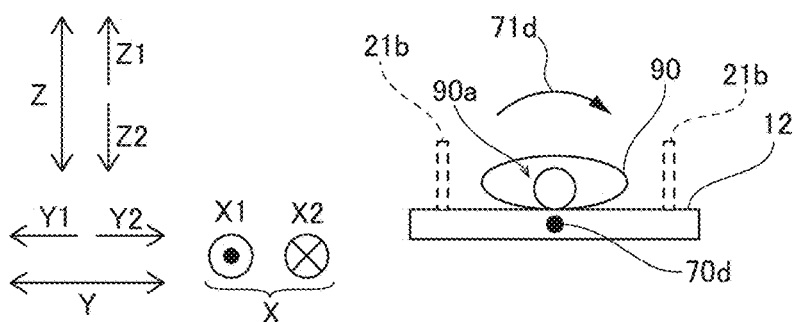
FIG. 11 is a schematic diagram for explaining a configuration in which the controller according to one embodiment sets the other of the rotation directions with the head-foot direction as an axis to the movement-prohibited direction.

FIG. 11 is a schematic diagram of the table top 12 on which the subject 90 is placed, as viewed from the X1-direction side. As shown in FIG. 11, the table top 12 has no shoulder rest 21*a* (see FIG. 8) or stepping platform 21*c* (see FIG. 9). Further, in the example shown in FIG. 11, the grip bar 21*b* is positioned on the table top 12 near the foot 90*b* of the subject 90 (see FIG. 9). In other words, the grip bar 21*b* is arranged at a position where the subject 90 cannot grip. Note that in FIG. 11, the grip bar 21*b* is shown with a dashed line to indicate that the subject 90 is unable to grip it. As shown in FIG. 11, in the case where the grip bar 21*b* is not located at a position where the subject 90 can grip, when the table top 12 is tilted in the direction indicated by the arrow 71*d* centered on the rotation center 70*d*, the position of the subject 90 on the table top 12 may shift due to the tilting of the table top 12. Therefore, the controller 16 sets the rotation direction about the X-axis as the movement-prohibited direction 52 in a case where the grip bar 21*b* is not positioned at a position where the subject 90 can grip.

(Restriction on Movement of Table Top Driving Mechanism)

In this embodiment, the controller 16 is configured to acquire the movement-prohibited direction 52 (see FIG. 7), which is the direction in which the subject holding member 21 is not provided, based on the presence or absence of the subject holding member 21 (see FIG. 5) acquired by the image processing unit 15 (see FIG. 1). Further, in this embodiment, the controller 16 is configured to determine whether the direction of tilting the table top 12 (see FIG. 2) by the table top driving mechanism 13 (see FIG. 2) and the movement-prohibited direction 52 coincide. Further, the controller 16 is configured to perform at least one of restring the operation of the table top driving mechanism 13 and notifying that the direction of tilting the table top 12 and the movement-prohibited direction 52 coincide, when the direction of tilting the table top 12 and the movement-prohibited direction 52 coincide.

In this embodiment, the controller 16 is configured to restrict the operation of the table top 12 by the table top driving mechanism 13 when the direction of tilting the table top 12 and the movement-prohibited direction 52 coincide. Specifically, the controller 16 is configured to restrict the operation of the table top 12 by the table top driving mechanism 13 by prohibiting the operation of the table top 12 by the table top driving mechanism 13 or by reducing the tilting speed of the table top 12 by the table top driving mechanism 13. More specifically, the controller 16 is configured to restrict the operation of the table top 12 by the table top driving mechanism 13 by prohibiting the tilting of the table top 12 by the table top driving mechanism 13. In other words, in this embodiment, the controller 16 performs control not to move the table top 12 even when there is an operation input to tilt the table top 12 in the movement-prohibited direction 52.

Here, depending on the facility, such as a hospital, using the X-ray imaging apparatus 1 (see FIG. 1), a doctor or other person may wish to tilt the table top 12 in the movement-prohibited direction 52 when the doctor or other person is in the vicinity of the X-ray imaging apparatus 1. For example, even in the case where the stepping platform 21*c* (see FIG. 5) is not provided, a doctor or other person may desire to tilt the table top 12 when the angle of tilting the table top 12 is small. Therefore, in this embodiment, the controller 16 is configured to allow the operation of the table top 12 in the movement-prohibited direction 52 if the operation in the movement-prohibited direction 52 is permitted in the relation 51 (see FIG. 1) between the type of the subject holding member 21 stored in the storage unit 17 (see FIG. 1) and the direction of tilting the table top 12, even in the case where the direction of tilting the table top 12 and the movement-prohibited direction 52 coincide.

In this embodiment, the controller 16 is configured to store the relation 51 between the type of the subject holding member 21 and the direction of tilting the table top 12 in advance, based on the operation input of the operator. Note that the relation 51 between the type of the subject holding member 21 and the direction of tilting the table top 12 refers to the information indicating the relation between the subject holding member 21 and the direction of tiling the table top 12 in order to permit the movement of the table top 12 to a direction that would normally be set as the movement-prohibited direction 52. For example, when allowing the movement of the table top 12 with respect to the titling direction even in the case where the stepping platform 21*c* is not provided on the foot 90*b* side of the subject 90, the controller 16 stores in the storage unit 17 information that allows the movement of the table top 12 with respect to the tilting direction even in the case where the stepping platform 21*c* is not provided, as the relation 51 between the type of subject holding member 21 and the direction of tilting the table top 12.

(Notification That Direction of Tilting Table Top and Movement-Prohibited Direction Coincide)

Further, in this embodiment, the controller 16 is configured to notify that the direction of tilting the table top 12 and the movement-prohibited direction 52 coincide. In this embodiment, when the direction of tilting the table top 12 coincides with the movement-prohibited direction 52 and there is an input operation to move the table top 12 via the table top driving mechanism 13, the controller 16 restricts the operation of the table top 12 by the table top driving mechanism 13 and notifies that the direction of tilting the table top 12 coincides with the movement-prohibited direction 52. Specifically, the controller 16 is configured to notify on the display unit 18 that the direction of tilting the table top 12 coincides with the movement-prohibited direction 52, thereby indicating that the direction of tilting the table top 12 and the movement-prohibited direction 52 coincide.

Figure 12:
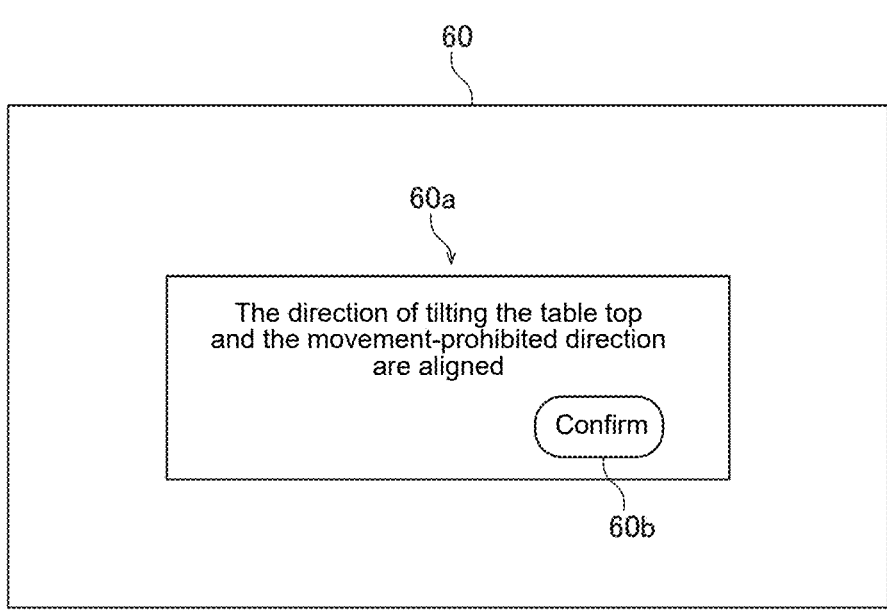
FIG. 12 is a schematic diagram for explaining a configuration in which a controller according to one embodiment notifies that the direction of tilting the table top and the movement-prohibited direction coincide.

More specifically, as shown in FIG. 12, the controller 16 (see FIG. 1) displays a screen 60 in the display unit 18 (see FIG. 1) indicating that the direction of tilting the table top 12 (see FIG. 1) and the movement-prohibited direction 52 (see FIG. 1) coincide, thereby notifying that the direction of tilting the table top 12 and the movement-prohibited direction 52 coincide. In this embodiment, the controller 16 is configured to display the screen 60 on both the first display unit 18*a* and the second display unit 18*b*. Note that the controller 16 may be configured to display the screen 60 in either the first display unit 18*a* or the second display unit 18*b*.

As shown in FIG. 12, the screen 60 displays a message 60*a* indicating that the direction of tilting the table top 12 and the movement-prohibited direction 52 coincide, and a confirmation button 60*b*.

The confirmation button 60*b* is a GUI (Graphical User Interface) push button. When the confirmation button 60*b* is pressed, the controller 16 determines that the operator has confirmed the message 60*a*.

(Releasing Restriction of Movement of Table Top)

In this embodiment, the controller 16 is configured to continue to prohibit the table top driving mechanism 13 from tilting the table top 12 until it receives an input operation from the operator to release the restriction on the movement of the table top 12 after prohibiting the movement of tilting the table top 12. For example, when the confirmation button 60*b* shown on the screen 60 is pressed, the controller 16 determines that an operation input to release the restriction on the operation of the table top 12 has been made, and releases the prohibition on the operation of tilting the table top 12 by the table top driving mechanism 13.

Note that the controller 16 may release the prohibition of the operation of tilting the table top 12 by the table top driving mechanism 13 based on the fact that the operator has once removed his/her hand from the first input reception unit 20 (see FIG. 1) or the second input reception unit 201 (see FIG. 1) and then again made an operation input using the first input reception unit 20 or the second input reception unit 201. The controller 16 may be configured to release the prohibition of the movement of tilting the table top 12 by the table top driving mechanism 13 when the operator performs an intended operation.

(Processing to Control Operation of Table Top)

Figure 13:
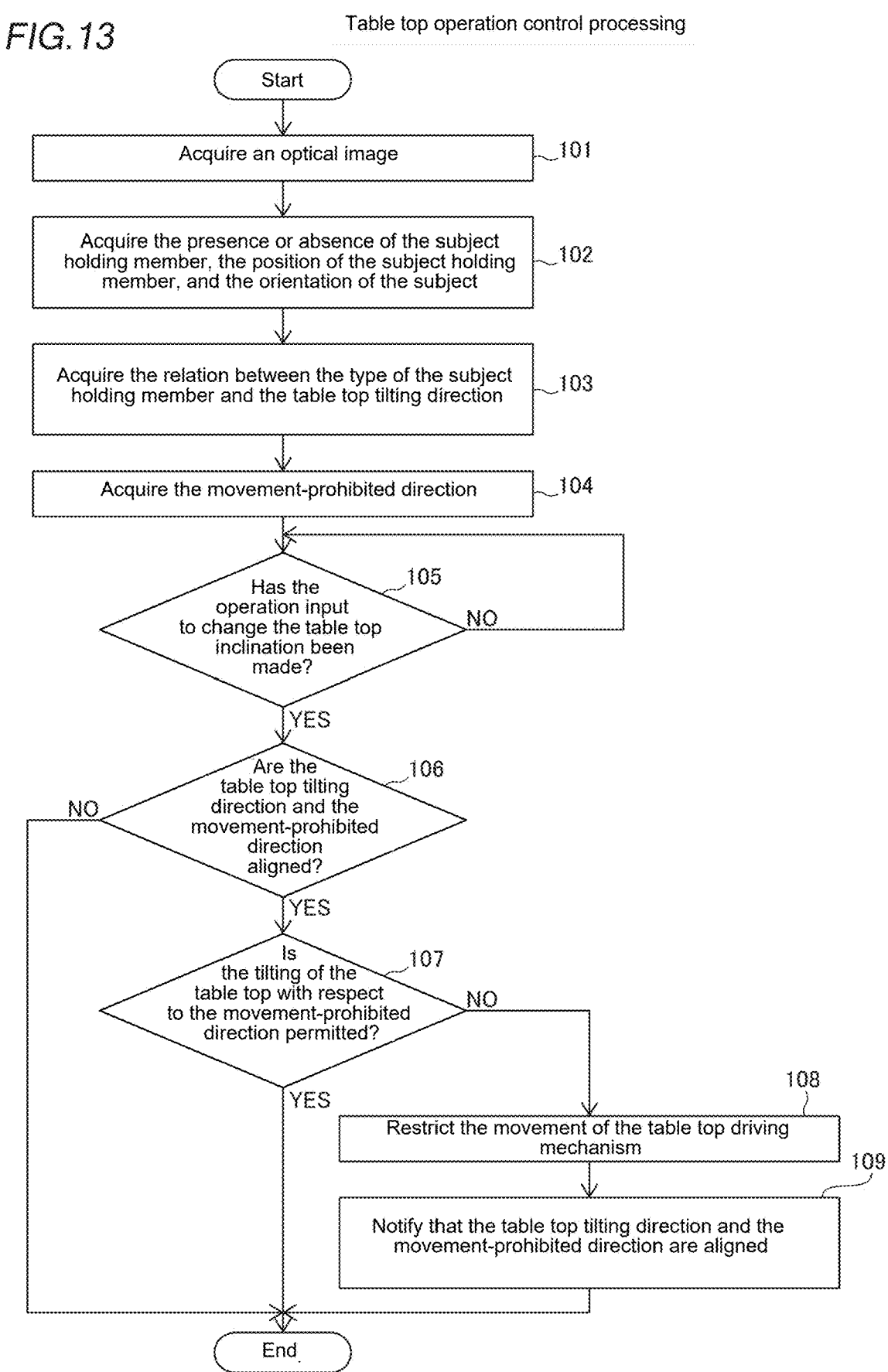
FIG. 13 is a flowchart for explaining the control processing in which an X-ray imaging apparatus according to one embodiment controls the operation of the table top.

Next, referring to FIG. 13, the processing to control the operation of the table top 12 (FIG. 2) by the X-ray imaging apparatus 1 (see FIG. 1) according to this embodiment will be described.

In Step 101, the imaging unit 14 (see FIG. 1) acquires an optical image 30 (see FIG. 5). Specifically, the imaging unit 14 captures an optical image 30 showing the subject holding member 21 (see FIG. 5) and the subject 90 (see FIG. 5).

In Step 102, the image processing unit 15 (see FIG. 6) acquires the presence or absence of the subject holding member 21. Specifically, as shown in FIG. 6, the image processing unit 15 acquires the presence or absence of the subject holding member 21 based on the optical image 30 and the trained model 40. In this embodiment, the image processing unit 15 acquires the information 50 on the presence or absence of the subject holding member 21. Note that in the case where the information 50 on the presence or absence of the subject holding member 21 has been acquired and stored in the storage unit 17, the image processing unit 15 may acquire the information 50 on the presence or absence of the subject holding member 21 from the storage unit 17.

Further, in Step 102, the image processing unit 15 acquires the position of the subject holding member 21. Specifically, the image processing unit 15 acquires the information 53 on the position of the subject holding member 21 based on the optical image 30 and the trained model 40. Note that in the case where the information 53 on the position of the subject holding member 21 has been stored in the storage unit 17, the image processing unit 15 may acquire the information 53 on the position of the subject holding member 21 from the storage unit 17.

Further, in Step 102, the image processing unit 15 acquires the information 54 on the orientation of the subject 90. Specifically, the image processing unit 15 acquires the information 54 on the orientation of the subject 90 based on the optical image 30 and the trained model 40. Note that in the case where the information 54 on the orientation of the subject 90 has been stored in the storage unit 17, the image processing unit 15 may acquire the information 54 on the orientation of the subject 90 from the storage unit 17.

In Step 103, the controller 16 (see FIG. 1) acquires the relation 51 (see FIG. 1) between the type of the subject holding member 21 and the direction of tilting the table top 12. Specifically, the controller 16 acquires the relation 51 between the type of the subject holding member 21 stored in the storage unit 17 (see FIG. 1) and the direction of tilting the table top 12.

Figure 7:
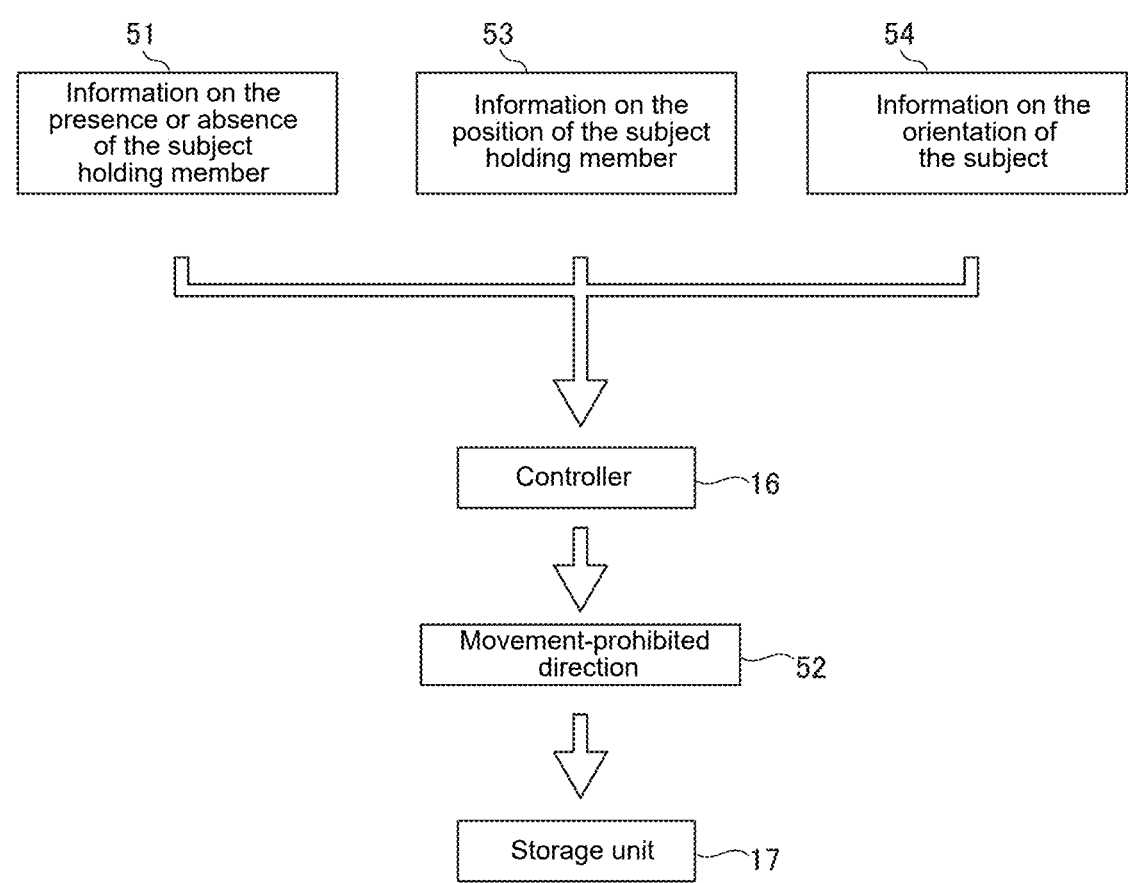
FIG. 7 is a schematic diagram for explaining a configuration in which a controller according to one embodiment acquire a movement-prohibited direction.

In Step 104, the controller 16 acquires the movement-prohibited direction 52 (see FIG. 7). Specifically, as shown in FIG. 7, the controller 16 acquires the movement-prohibited direction 52 based on the information 50 on the presence or absence of the subject holding member 21, the information 53 on the position of the subject holding member 21, and the information 54 on the direction of the subject 90. Note that in the case where the movement-prohibited direction 52 is stored in the storage unit 17, the controller 16 may acquire the movement-prohibited direction 52 from the storage unit 17.

In Step 105, the controller 16 determines whether there is an operation input to change the tilt of the table top 12. If there is an input operation to change the tilt of the table top 12, the processing proceeds to Step 106. If there is no input operation to change the tilt of the table top 12, the processing of Step 105 is repeated.

In Step 106, the controller 16 determines whether the direction of tilting the table top 12 and the movement-prohibited direction 52 coincide. If the direction of tilting the table top 12 coincides with the movement-prohibited direction 52, the processing proceeds to Step 107. If the direction of tilting the table top 12 does not coincide with the movement-prohibited direction 52, the processing is terminated. In other words, if the direction of tilting the table top 12 does not coincide with the movement-prohibited direction 52, the controller 16 tilts the table top 12 based on the operation input.

In Step 107, the controller 16 determines whether tilting the table top 12 in the movement-prohibited direction 52 is permitted. Specifically, the controller 16 determines whether the table top 12 is allowed to be tilted in the movement-prohibited direction 52 based on the relation 51 between the movement-prohibited direction 52, the type of the subject holding member 21, and the direction 52 of tilting the table top 12. In the case where it is permitted to tilt the table top 12 in the movement-prohibited direction 52, the processing is terminated. In other words, in the case where it is permitted to tilt the table top 12 in the movement-prohibited direction 52, the controller 16 tilts the table top 12 based on the operation input. In the case where it is not permitted to tilt the table top 12 in the movement-prohibited direction 52, the processing proceeds to Step 108.

In Step 108, the controller 16 restricts the operation of the table top driving mechanism 13 (see FIG. 1). In this embodiment, the controller 16 restricts the operation of the table top driving mechanism 13 by prohibiting the operation.

In Step 109, the controller 16 notifies that the direction of tilting the table top 12 and the movement-prohibited direction 52 coincide. Specifically, the controller 16 notifies on the display unit 18 (see FIG. 1) that the direction of tilting the table top 12 coincides with the movement-prohibited direction 52 by displaying the message 60*a* (see FIF. 12) indicating that the direction of tilting the table top 12 and the movement-prohibited direction 52 coincide, thereby indicating that the direction of tilting the table top 12 and the movement-prohibited direction 52 coincide. Thereafter, the processing is terminated.

Note that either the processing of Step 103 or the processing of Step 104 may be performed first.

Figure 14:
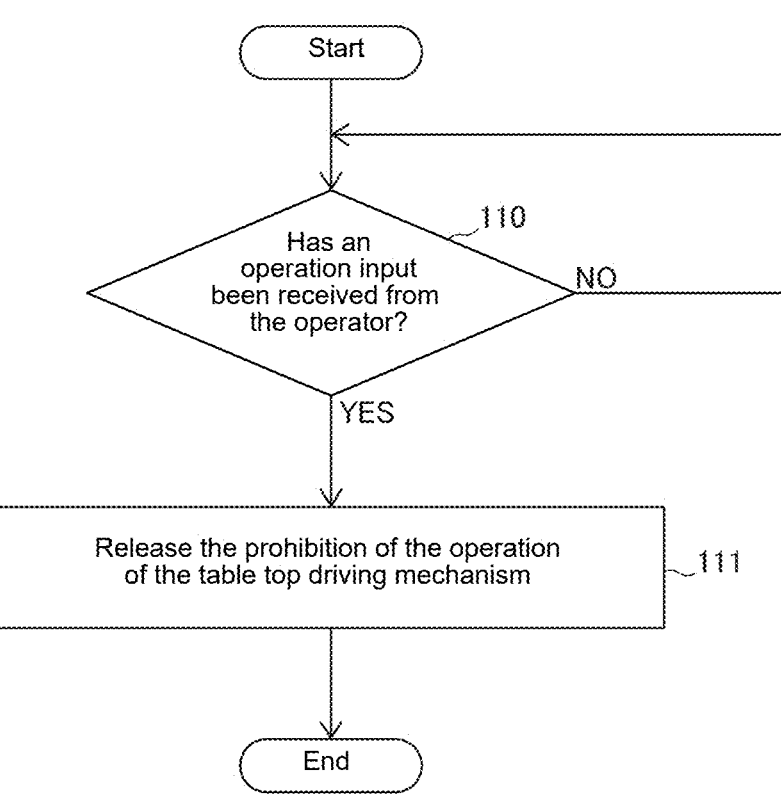
FIG. 14 is a flowchart for explaining the processing in which a controller according to one embodiment releases the prohibition on the operation of the table top driving mechanism.

Next, referring to FIG. 14, the processing for the controller 16 (see FIG. 1) to release the restriction on the operation of the table top driving mechanism 13 (see FIG. 1) will be described.

In Step 110, the controller 16 determines whether there is an operation input from the operator. Specifically, the controller 16 determines whether the confirmation button 60*b* on the screen 60 shown in FIG. 12 has been pressed. Note that the controller 16 may determine whether there is an operation input by the first input reception unit 20 or the second input reception unit 201 again after the hand is detached from the first input reception unit 20 (see FIG. 1) or the second input reception unit 201 (see FIG. 1). If there is an operation input from the operator, the processing proceeds to Step 111. If there is no operation input from the operator, the processing of Step 110 is repeated.

In Step 111, the controller 16 releases the restriction on the operation of the table top driving mechanism 13. Specifically, the controller 16 releases the prohibition on operation of the table top driving mechanism 13. Thereafter, the processing is terminated.

(Effects of this Embodiment)

In this embodiment, the following effects can be obtained.

In this embodiment, as described above, the X-ray imaging apparatus 1 is provided with: X-ray irradiation unit 10 configured to emit X-rays; the X-ray detector 11 configured to detect X-rays emitted from the X-ray irradiation unit 10; a table top 12 configured to place the subject 90 thereon; and a table top driving mechanism 13 configured to change a tilt of the table top 12; an imaging unit 14 configured to image a subject 90 placed on the table top 12 and a subject holding member 21 provided on the table top 12 to hold a posture of the subject 90; an image processing unit 15 configured to acquire presence or absence of the subject holding member 21, based on an image (the optical image 30) of the subject 90 and the subject holding member 21 captured by the imaging unit 14; and a controller 16, wherein the controller 16 is configured to acquire a movement-prohibited direction 52 which is a direction in which the subject holding member 21 is not arranged, based on the presence or absence of the subject holding member 21 acquired by the image processing unit 15, determine whether a direction of tilting the table top 12 by the table top driving mechanism 13 and the movement-prohibited direction 52 coincide, and perform, when the direction of tilting the table top 12 and the movement-prohibited direction 52 coincide, at least one of restricting an operation of the table top driving mechanism 13 and notifying that the direction of tilting the table top 12 and the movement-prohibited direction coincide.

With this configuration, when an operation input to tilt the table top 12 in the direction that coincides with the movement-prohibited direction 52 is received, the operation of the table top driving mechanism 13 is restricted, or it is notified that the direction of tilting the table top 12 and the movement-prohibited direction 52 coincide. In the case where the movement of the table top driving mechanism 13 is restricted, it is possible to prevent the table top 12 from tilting to an angle at which the subject's position on the table top 12 shifts. Further, in the case where it is notified that the direction of tilting the table top 12 and the movement-prohibited direction 52 coincide, it becomes possible to make the operator aware of the possibility that the position of the subject 90 on the table top 12 may shift. This can prompt the operator to stop the operation of the table top driving mechanism 13. As a result, it is possible to suppress the shifting of the position of the subject 90 on the table top 12 due to the tilting of the table top 12 in a predetermined direction.

Further, in this embodiment, as described above, the X-ray imaging system 100 includes: an X-ray irradiation unit 10 configured to emit X-rays; an X-ray detector 11 configured to detect X-rays emitted from the X-ray irradiation unit 10; a table top 12 configured to place the subject 90 thereon; and a table top driving mechanism 13 configured to change a tilt of the table top 12; an imaging unit 14 configured to image a subject 90 placed on the table top 12 and a subject holding member 21 provided on the table top 12 to hold a posture of the subject 90; an image processing unit 15 configured to acquire presence or absence of the subject holding member 21, based on an image (the optical image 30) of the subject 90 and the subject holding member 21 captured by the imaging unit 14; and a controller 16, wherein the controller 16 is configured to acquire a movement-prohibited direction 52 which is a direction in which the subject holding member 21 is not provided, based on the presence or absence of the subject holding member 21 acquired by the image acquisition acquisition processing unit 15, determine whether a direction of tilting the table top 12 by the table top driving mechanism 13 and the movement-prohibited direction 52 coincide, and perform, when the direction of tilting the table top 12 and the movement-prohibited direction 52 coincide, at least one of restricting an operation of the table top driving mechanism 13 and notifying that the direction of tilting the table top 12 and the movement-prohibited direction 52 coincide.

With this, in the same manner as the X-ray imaging apparatus 1, it is possible to provide an X-ray imaging system 100 capable of suppressing the shifting of the position of the subject 90 on the table top 12 due to the tilting of the table top 12 in a predetermined direction.

Further, in the above-described embodiment, the following further effects can be obtained by configuring as follows.

That is, in this embodiment, as described above, in the case where the direction of tilting the table top 12 coincides with the movement-prohibited direction 52, the controller 16 restricts the operation of the table top 12 by the table top driving mechanism 13 and notifies that the direction of tilting the table top 12 coincides with the movement-prohibited direction 52. With this, the operation of the table top 12 is restricted, and it is possible for the operator to realize that the direction of tilting the table top 12 coincides with the movement-prohibited direction 52, and that there is a possibility that the position of the subject 90 on the table top 12 may shift due to the tilting of the table top 12. As a result, since it is possible to make the operator realize that the direction of tilting the table top 12 coincides with the movement-prohibited direction 52 in a state in which the operation of the table top driving mechanism 13 is restricted, the shifting of the subject 90 on the table top 12 can be suppressed more effectively.

Further, in this embodiment, as described above, the subject holding member 21 includes at least one of the shoulder rest 21a, the grab bar 21b, and the stepping platform 21c. The image processing unit 15 is configured to acquire the presence or absence of the subject holding member 21 by acquiring whether at least one of the shoulder rest 21a, the grip bar 21b, and the stepping platform 21c is provided on the table top 12. The controller 16 is configured to determine whether the subject holding member 21 corresponding to the shoulder rest 21a, the grip bar 21b, and the stepping platform 21c is provided at the position corresponding to the direction of tilting the table top 12, and to set the direction in which the subject holding member 21 corresponding to the shoulder rest 21a, the grip bar 21b, and the stepping platform 21c is not provided at the position corresponding to the direction of tilting the table top 12, as the movement-prohibited direction 52.

With this, the direction in which the shoulder rest 21a, the grip bar 21b, and the stepping platform 21c are not provided is set as the movement-prohibited direction 52. Therefore, in the X-ray imaging apparatus 1 in which the subject holding member 21, including at least one of the shoulder rest 21a, the grip bar 21b, and the stepping platform 21c, is provided for imaging, it is possible to easily suppress the shifting of the position of the subject 90 on the table top 12 due to the tilting of the table top 12 in the direction in which the subject holding member 21, including one of the shoulder rest 21a, the grip bar 21b, and the stepping platform 21c, is not provided.

Further, in this embodiment, as described above, the image processing unit 15 is configured to acquire the orientation of the subject 90 on the table top 12 and the position of the subject holding member 21, as well as the presence or absence of the subject holding member 21, based on the image (optical image 30) of the subject 90 and the subject holding member 21 captured by the imaging unit 14. The controller 16 is configured to set the movement-prohibited direction 52 based on the orientation of the subject 90 on the table top 12 and the presence or absence and the position of the subject holding member 21.

Here, when imaging the subject 90, there are cases where the subject 90 is placed on the table top 12 with the head-foot direction of the subject 90 facing the opposite direction. In this case, the subject holding member 21 must be positioned according to the orientation of the subject 90. Further, depending on the height of the subject 90, the position of the subject holding member 21 needs to be adjusted. Therefore, as described above, by setting the movement-prohibited direction 52 based on the orientation of the subject 90 on the table top 12 and the position of the subject holding member 21, as well as the presence of the subject holding member 21, the movement-prohibited direction 52 can be set more precisely according to the orientation of the subject 90 and the position of the subject holding member 21. As a result, it is possible to more effectively suppress the shifting of the position of the subject 90 on the table top 12. Further, in the case where the operator can manually change the position of the subject holding member 21, it is necessary to install multiple distance sensors and other components according to the positions where the subject holding member 21 can be attached, which increases the number of parts. Further, depending on the position at which the subject holding member 21 is moved, it may not be possible to acquire the position with a distance sensor or other means. Therefore, by configuring the image processing unit 15 so as to acquire the position of the subject holding member 21 based on the optical image 30 as described above, even in the case where the position of the subject holding member 21 is manually moved by the operator, the position of the subject holding member 21 can be easily acquired while suppressing the increase in the number of parts.

Further, in this embodiment, as described above, the controller 16 is configured to restrict the movement of the table top 12 by the table top driving mechanism 13 by either prohibiting the operation of tilting the table top 12 by the table top driving mechanism 13 or by reducing the tilting speed of the table top 12 by the table top driving mechanism 13.

With this, in the case where the controller 16 prohibits the operation of tilting the table top 12 by the table top driving mechanism 13, it is possible to prevent the table top 12 from tilting in the movement-prohibited direction 52. As a result, it is possible to reliably suppress the shifting of the position of the subject 90 on the table top 12. Further, in the case where the controller 16 decreases the tilting speed of the table top by the table top driving mechanism 13, the time required for the table top 12 to be tilted to an angle at which the position of the subject 90 on the table top 12 shifts can be increased. As a result, the operator can stop the operation of the table top driving mechanism 13 until the position of the subject 90 on the table top 12 shifts. Therefore, it is possible to further suppress the shifting of the position of the subject 90 on the table top 12 due to the tilting of the table top 12 in a predetermined direction.

Further, in this embodiment, as described above, the controller 16 is configured to restrict the operation of the table top 12 by the table top driving mechanism 13 by prohibiting such operation, and continues to enforce this prohibition until it receives an input from the operator to release the restriction on the movement of the table top 12 after the tilting operation has been prohibited.

With this, the operation of the table top driving mechanism 13 is prohibited until the operator intentionally inputs an operation to release the restriction on the movement of the table top 12. This prevents the table top 12 from resuming the movement and tilting in a predetermined direction until the operator has confirmed the status of the subject 90, thus preventing any displacement of the subject 90 on the table top 12.

Further, in this embodiment, as described above, in the case where the direction of tilting the table top 12 coincides with the movement-prohibited direction 52, the controller 16 is configured to restrict the operation of the table top 12 by the table top driving mechanism 13 and to notify that the direction of tilting the table top 12 and the movement-prohibited direction 52 coincide, after receiving an operation input to move the table top 12.

Here, if the operator is informed in advance that there is a movement-prohibited direction 52, it may interfere with the operator's work, such as checking the X-ray image. Therefore, by configuring as described above, when the operator performs an operation input to operate the table top driving mechanism 13, the operator is informed that the direction of tilting the table top 12 coincides with the movement-prohibited direction 52, so that the operator can grip that the position of the subject 90 on the table top 12 may shift without disturbing the operator's work. As a result, the user's convenience (usability) can be improved.

Further, in this embodiment, as described above, the image processing unit 15 is configured to acquire the position of the subject holding member 21 by the trained model 40 that has been trained to acquire the position of the subject holding member 21 on the table top 12. With this, it is possible to easily and accurately acquire the position of the subject holding member 21 based on the image (the optical image 30) in which the subject 90 and the subject holding member 21 are shown.

Further, as described above, in this embodiment, it is further provided with the storage unit 17 that stores the relation 51 between the type of the subject holding member 21 and the direction of tilting the table top 12. The controller 16 is configured to store the relation 51 between the type of the subject holding member 21 and the direction of tilting the table top 12 in the storage unit 17 based on the input operation of the operator, and allow the operation of the table top 12 in the movement-prohibited direction 52 in the relation 51 between the type of the subject holding member 21 stored in the storage unit 17 and the direction of tilting the table top 12 even in the case where the direction of tilting the table top 12 and the movement-prohibited direction 52 coincide.

Here, in a facility (such as a hospital) where the X-ray imaging apparatus 1 is used, it may be permissible to tilt the table top 12 in a direction in which the subject holding member 21 is not located, when the operator is in the vicinity of the X-ray imaging apparatus 1. Further, if the grip bar 21*b* is provided on one side of the table top 12, it may be permissible to tilt the table top 12 in the direction in which the grip bar 21*b* is not provided. Therefore, as described above, by storing the relation 51 between the type of the subject holding member 21 and the direction of tilting the table top 12, it is possible to set the conditions that allow tilting the table top 12 in the movement-prohibited direction 52 for each facility using the X-ray imaging apparatus 1. As a result, it becomes possible to tilt the table top 12 in the movement-prohibited direction 52 according to the relation 51 between the type of the subject holding member 21 and the direction of tilting the table top 12, thus improving the convenience (usability) of the operator.

Further, in this embodiment, as described above, the imaging unit 14 is provided at the position facing the table top 12 in the housing 10*a* of the X-ray irradiation unit 10. Here, in the case where the imaging unit 14 is mounted on a ceiling of an examination room, depending on the relative position between the imaging unit 14 and the X-ray irradiation unit 10, the housing 10*a* of the X-ray irradiation unit 10 may block the imaging field of view of the imaging unit 14. As a result, in the image (the optical image 30) capturing the subject 90 and the subject holding member 21, it may be difficult to accurately determine the presence or absence of the subject holding member 21. Therefore, by configuring as described above, it is possible to prevent the imaging field of view of the imaging unit 14 from being obstructed by the housing 10*a* of the X-ray irradiation unit 10 or other parts of the system. As a result, it becomes possible to accurately determine the presence or absence of the subject holding member 21, etc., in the image (the optical image 30) in which the subject 90 and the subject holding member 21 are captured, so that the movement-prohibited direction 52 can be set with high accuracy.

Further, as described above, the image processing unit 15 is configured to generate the X-ray image 31 based on the X-rays detected by the X-ray detector 11, and is further provided with the display unit 18 that displays the X-ray image 31. The controller 16 is configured to notify that the direction of tilting the table top 12 coincides with the movement-prohibited direction 52 by displaying on the display unit 18 that the direction of tilting the table top 12 coincides with the movement-prohibited direction 52.

With this, in the display unit 18, it is displayed that the direction of tilting the table top 12 coincides with the movement-prohibited direction 52. Therefore, it is possible for the operator to visually recognize that the position of the subject 90 on the table top 12 may shift. Therefore, the operator can visually recognize that the position of the subject 90 on the table top 12 may shift due to the tilt of the table top 12 in a predetermined direction. As a result, it is possible to ensure that the operator performs actions to prevent the position of the subject 90 on the table top 12 from shifting, such as stopping the operation of the table top driving mechanism 13.

Further, as described above, the image processing unit 15 is configured to generate the X-ray image 31 based on the X-rays detected by the X-ray detector 11, and is further provided with the display unit 18 that displays the X-ray image 31. The controller 16 is configured to notify that the direction of tilting the table top 12 coincides with the movement-prohibited direction 52 by displaying on the display unit 18 that the direction of tilting the table top 12 coincides with the movement-prohibited direction 52.

This makes it possible to provide an X-ray imaging system 100 that, like the X-ray imaging apparatus 1, allows the operator to reliably perform actions to suppress the shifting of the position of the subject 90 on the table top 12, such as stopping the operation of the table top driving mechanism 13.

<Modifications>

Note that the embodiments disclosed here should be considered illustrative and not restrictive in all respects. It should be noted that the scope of the invention is indicated by claims and is intended to include all modifications (modified examples) within the meaning and scope of the claims and equivalents.

That is, in this embodiment, an example is shown in which in the case where the direction of tilting the table top 12 coincides with the movement-prohibited direction 52, the controller 16 restricts the operation of the table top 12 by the table top driving mechanism 13 and notifies that the direction of tilting the table top 12 coincides with the movement-prohibited direction 52, but the present invention is not limited thereto. For example, when the direction of tilting the table top 12 and the movement-prohibited direction 52 coincide, the controller may be configured to perform either the restriction of the operation of the table top driving mechanism 13 or the notification that the direction of tilting the table top 12 and the movement-prohibited direction 52 coincide. However, by performing both the restriction of the operation of the table top driving mechanism 13 and the notification that the direction of tilting the table top 12 coincides with the movement-prohibited direction 52, it is possible to further suppress the shifting of the position of the subject 90 on the table top 12 due to the tilting of the table top 12. Therefore, in the case where the direction of tilting the table top 12 coincides with the movement-prohibited direction 52, the controller 16 is preferably configured to restrict the operation of the table top 12 by the table top driving mechanism 13 and to notify that the direction of tilting the table top 12 coincides with the movement-prohibited direction 52.

Further, in the above-described embodiment, an example is shown in which the subject holding member 21 includes all of the shoulder rest 21a, the grip bar 21b, and the stepping platform 21c, but the present invention is not limited thereto. It is sufficient that the subject holding member 21 includes one of the shoulder rest 21a, the grip bar 21b, and the stepping platform 21c, depending on the direction of tilting the table top 12. Further, it is sufficient that the controller 16 acquires the movement-prohibited direction 52 based on a member corresponding to the direction of tilting the table top 12, out of the shoulder rest 21a, the grip bar 21b, and the stepping platform 21c.

Further, in the above-described embodiment, an example is shown in which the controller 16 sets the movement-prohibited direction 52 based on the orientation of the subject 90 and the presence and absence and the position of the subject holding member 21, but the present invention is not limited thereto. The controller may be configured to set the movement-prohibited direction 52 without basing it on the orientation of the subject 90 and the position of the subject holding member 21, as long as it is based at least on the presence or absence of the subject holding member 21. However, by setting the movement-prohibited direction 52 based on the orientation of the subject 90 and the position of the subject holding member 21, as well as the presence or absence of the subject holding member 21, the movement-prohibited direction 52 can be set more accurately. Therefore, the controller 16 is preferably configured to set the movement-prohibited direction 52 based on the orientation of the subject 90 on the table top 12, and the presence or absence and the position of the subject holding member 21.

Further, in this embodiment, an example is shown in which the controller 16 restricts the operation of the table top driving mechanism 13 by prohibiting the operation, but the present invention is not limited thereto. For example, the controller 16 may be configured to restrict the operation of the table top driving mechanism 13 by lowering the rate of tilting the table top 12 by the table top driving mechanism 13. In this case, the controller 16 may decrease the rate of tilting the table top 12 by the table top driving mechanism 13 so that the operator can stop the operation of the table top driving mechanism 13 before the table top 12 tilts to an angle at which the position of the subject 90 on the table top 12 may shift.

Further, in the above-described embodiment, an example is shown in which the controller 16 prohibits the operation of tilting the table top 12 by the table top driving mechanism 13 until receiving an operation input to release the restriction of the operation of the table top 12 by the operator, after the operation of tilting the table top 12 is prohibited. For example, the controller may be configured to prohibit the operation of tilting the table top 12 by the table top driving mechanism 13 until a predetermined amount of time has elapsed after the table top 12 tilting operation is prohibited.

Here, in the configuration that the controller prohibits the operation of tilting the table top 12 and then prohibits the operation of tilting the table top by the table top driving mechanism 13 until a predetermined time elapses, there may be cases where the prohibition of the operation of the table top driving mechanism 13 is unintentionally released. Therefore, the controller 16 is preferably configured to prohibit the operation of tilting the table top 12 by the table top driving mechanism 13 until it receives an operation input to release the restriction on the operation of the table top 12 by the operator after prohibiting the operation of tilting the table top 12.

Further, in this embodiment, an example is shown in which, when the direction of tilting the table top 12 coincides with the movement-prohibited direction 52, after receiving an operation input to move the table top 12, the operation of tilting the table top 12 by the table top driving mechanism 13 is restricted, and a notification is issued that the direction of tilting the table top 12 coincides with the movement-prohibited direction 52. However, the present invention is not limited to this example. For example, the controller may be configured to notify by displaying the movement-prohibited direction 52 on the display unit 18 when it acquires the movement-prohibited direction 52.

In the case where the controller is configured to display the movement-prohibited direction 52 on the display unit 18 when it acquires the movement-prohibited direction 52, the movement-prohibited direction 52 will continue to be notified while the operator is checking the X-ray image 31 or other images on the display unit 18, which will interfere with the operator's work. Accordingly, in the case where the direction of tilting the table top 12 coincides with the movement-prohibited direction 52, it is preferably configured such that the controller 16 restricts the operation of the table top 12 by the table top driving mechanism 13 and notifies that the direction of tilting the table top 12 coincides with the movement-prohibited direction 52 after receiving an operation input to the table top driving mechanism 13 to move the table top 12.

Further, in the above-described embodiment, an example is shown in which the image processing unit 15 acquires the position of the subject holding member 21 by the trained model 40, but the present invention is not limited thereto. For example, the image processing unit 15 may be configured to acquire the position of the subject holding member 21 by pattern matching through image processing, without using the trained model 40.

Further, in the above-described embodiment, an example is shown in which even in the case where the direction of tilting the table top 12 coincides with the movement-prohibited direction 52, if the movement in the movement-prohibited direction 52 is permitted in the relation 51 between the type of the subject holding member 21 and the direction of inclining the table top 12, the controller 16 will allow the operation of the table top 12 in the movement-prohibited direction 52, but the present invention is not limited thereto. For example, the controller may be configured to prohibit the operation of the table top 12 in the movement-prohibited direction 52, not based on the relation 51 between the type of the subject holding member 21 and the direction of tilting the table top 12.

In this case, since the table top 12 does not move in the movement-prohibited direction 52, the shifting of the position of the subject 90 on the table top 12 can be further suppressed. Note that in the case where the operator is located in the vicinity of the X-ray imaging apparatus 1 and can immediately stop the table top driving mechanism 13, from the viewpoint of improving the convenience (usability) of the operator, the controller may be configured to operate the table top 12 in the movement-prohibited direction 52 if the movement in the movement-prohibited direction 52 is allowed.

Further, in the above-described embodiment, an example is shown in which the imaging unit 14 is provided at a position facing the table top 12 in the housing 10a of the X-ray irradiation unit 10, but the present invention is not limited thereto. The arrangement of the imaging unit 14 is not limited as long as it is possible to image the subject 90 placed on the table top 12 and the subject holding member 21.

Further, in the above-described embodiment, an example is shown in which the X-ray imaging apparatus 1 is provided with only one imaging unit 14, but the present invention is not limited thereto. In the case of imaging by one imaging unit 14, a plurality of imaging units may be provided when the subject 90 and the subject holding member 21 do not fit in the imaging field of view. For example, the X-ray imaging apparatus 1 may be provided with two imaging units arranged at one side and the other side of the housing 10a of the X-ray irradiation unit 10.

Further, the above-described embodiment, an example is shown in which the controller 16 notifies that the direction of tilting the table top 12 and the movement-prohibited direction 52 coincide by displaying on the display unit 18 that the direction of tilting the table top 12 and the movement-prohibited direction 52 coincide, but the present invention is not limited thereto. For example, the controller may be configured to notify that the direction of tilting the table top 12 and the movement-prohibited direction 52 coincide by using voice or light.

Further, in the above-described embodiment, an example is shown in which the X-ray imaging apparatus 1 is equipped with the display unit 18 (the first display unit 18a), but the present invention is not limited thereto. For example, the X-ray imaging apparatus 1 may not be equipped with the display unit 18. In this case, the X-ray imaging system 100 may be equipped with a display device that displays the X-ray image 31 and other images.

Further, in the above-described embodiment, an example is shown in which the X-ray imaging system 100 is provided with the control console 200, but the present invention is not limited thereto. For example, the X-ray imaging system 100 may not be equipped with the control console 200. In this case, the operator can use the first input reception unit 20 provided on the X-ray imaging apparatus 1 to perform the operation of tilting the table top 12.

Further, in the above-described embodiment, an example is shown in which the image processing unit 15 acquires the presence or absence of the subject holding member 21 based on the optical image 30, but the present invention is not limited thereto. For example, it may be configured such that the X-ray imaging apparatus 1 is equipped with a sensor that detects the attachment or removal of the subject holding member 21, and the detection result of the sensor that detects the attachment or removal of the subject holding member 21 when acquiring the presence or absence of the subject holding member 21 based on the optical image 30 by the image processing unit 15.

Further, in the above-described embodiment, an example is shown in which the processing of restricting the operation of the table top driving mechanism 13 by the controller 16 and the processing of releasing the restriction of the operation of the table top driving mechanism 13 are described using a flow-driven flowchart in which processing is performed in sequence according to the processing flow, but the present invention is not limited thereto. In the present invention, the processing of restricting the operation of the table top driving mechanism 13 and the processing of releasing the restriction of the operation of the table top driving mechanism 13 may be performed by event-driven processing that executes processing on an event-by-event basis. In this case, it may be performed in a completely event-driven manner, or a combination of event-driven and flow-driven.

[Aspects]

It would be understood by those skilled in the art that the exemplary embodiments described above are specific examples of the following aspects.

(Item 1)

An X-ray imaging apparatus comprising:

an X-ray irradiation unit configured to emit X-rays;

an X-ray detector configured to detect X-rays emitted from the X-ray irradiation unit;

a table top configured to place a subject thereon;

a table top driving mechanism configured to change a tilt of the table top;

an imaging unit configured to image the subject placed on the table top and a subject holding member provided on the table top to hold a posture of the subject;

an image processing unit configured to acquire presence or absence of the subject holding member, based on an image of the subject and the subject holding member captured by the imaging unit; and a controller, wherein the controller is configured to acquire a movement-prohibited direction which is a direction in which the subject holding member is not provided, based on the presence or absence of the subject holding member acquired by the image acquisition acquisition processing unit, determine whether a direction of tilting the table top by the table top driving mechanism and the movement-prohibited direction coincide, and perform, when the direction of tilting the table top and the movement-prohibited direction coincide, at least one of restricting an operation of the table top driving mechanism and notifying that the direction of tilting the table top and the movement-prohibited direction coincide.

(Item 2)

The X-ray imaging apparatus as recited in the above-described Item 1, wherein when the direction of tilting the table top and the movement-prohibited direction coincide, the controller is configured to restrict the operation of the table top by the table top driving mechanism and to notify that the direction of tilting the table top and the movement-prohibited direction coincide.

(Item 3)

The X-ray imaging apparatus as recited in the above-described Item 1 or 2, wherein the subject holding member includes at least one of a shoulder rest, a grip bar, and a stepping platform, wherein the image processing unit is configured to acquire the presence or absence of the subject holding member by acquiring whether at least one of the shoulder rest, the grip bar, and the stepping platform is provided on the table top, and wherein the controller is configured to determine whether the subject holding member corresponding to one of the shoulder rest, the grip bar, and the stepping platform is provided at a position corresponding to the direction of tilting the table top, and set a direction in which the subject holding member corresponding to one of the shoulder rest, the grip bar, and the stepping platform is not provided at a position corresponding to the direction of tiling the table top, as the movement-prohibited direction.

(Item 4)

The X-ray imaging apparatus as recited in any one of the above-described Items 1 to 3, wherein the image processing unit is configured to acquire the presence or absence of the subject holding member, an orientation of the subject on the table top, and the position of the subject holding member, based on the image of the subject and the subject holding member captured by the imaging unit, and wherein the controller is configured to set the movement-prohibited direction based on the orientation of the subject on the table top, the presence or absence of the subject holding member, and the position of the subject holding member.

(Item 5)

The X-ray imaging apparatus as recited in any one of the above-described Items 1 to 4, wherein the controller is configured to restrict the operation of the table top by the table top driving mechanism by prohibiting the operation of the table top to be tilted by the table top driving mechanism or by reducing a speed of tilting the table top by the table top driving mechanism.

(Item 6)

The X-ray imaging apparatus as recited in the above-described Item 5, wherein the controller is configured to restrict the operation of the table top by the table top driving mechanism by prohibiting the operation of tilting the table top by the table top driving mechanism, and continue prohibiting the operation of tilting the table top by the table top driving mechanism until an operation input to release restricting the operation of the table top by the operator is received after prohibiting the operation of tilting the table top.

(Item 7)

The X-ray imaging apparatus as recited in any one of the above-described Items 1 to 6, wherein in a case in which the direction of tilting the table top is coincident with the movement-prohibited direction, the controller is configured to restrict the operation of the table top by the table top driving mechanism after receiving an operation input to the table top driving mechanism to move the table top, and notify that the direction of tilting the table top and the movement-prohibited direction coincide.

(Item 8)

The X-ray imaging apparatus as recited in any one of the above-described Items 1 to 7, wherein the image processing unit is configured to acquire the position of the subject holding member by a trained model that has been trained to acquire the position of the subject holding member on the table top.

(Item 9)

The X-ray imaging apparatus as recited in any one of the above-described Items 1 to 8, further comprising:

a storage unit configured to store a relation between a type of the subject holding member and the direction of tilting the table top, wherein the controller is configured to store the relation between the type of the subject holding member and the direction of tilting the table top in the storage unit, based on an operation input of an operator, and allow the operation of the table top in the movement-prohibited direction when the movement in the movement-prohibited direction is permitted in the relation between the type of the subject holding member and the direction of tilting the table top stored in the storage unit, even when the direction of tilting the table top and the movement-prohibited direction coincide.

(Item 10)

The X-ray imaging apparatus as recited in any one of the above-described Items 1 to 9, wherein the imaging unit is provided at a position facing the table top in the housing of the X-ray irradiation unit.

(Item 11)

The X-ray imaging apparatus as recited in any one of the above-described Items 1 to 10, wherein the image processing unit is configured to generate an X-ray image based on X-rays detected by the X-ray detector, wherein the X-ray imaging apparatus further comprises a display unit for displaying the X-ray image, and wherein the controller is configured to notify that the direction of tilting the table top and the movement-prohibited direction coincide by displaying in the display unit that the direction of tilting the table top and the movement-prohibited direction coincide.

(Item 12)

An X-ray imaging system comprising:

an X-ray irradiation unit configured to emit X-rays;

an X-ray detector configured to detect X-rays emitted from the X-ray irradiation unit;

a table top configured to place the subject thereon;

a table top driving mechanism configured to change a tilt of the table top;

an imaging unit configured to image a subject placed on the table top and a subject holding member provided on the table top to hold a posture of the subject;

an image processing unit configured to acquire presence or absence of the subject holding member, based on an image of the subject and the subject holding member captured by the imaging unit; and a controller, wherein the controller is configured to acquire a movement-prohibited direction which is a direction in which the subject holding member is not provided, based on the presence or absence of the subject holding member acquired by the image acquisition acquisition processing unit, determine whether a direction of tilting the table top by the table top driving mechanism and the movement-prohibited direction coincide, and perform, when the direction of tilting the table top and the movement-prohibited direction coincide, at least one of restricting an operation of the table top driving mechanism and notifying that the direction of tilting the table top and the movement-prohibited direction coincide.

(Item 13)

The X-ray imaging system as recited in the above-described Item 12, wherein the image processing unit is configured to generate an X-ray image based on X-rays detected by the X-ray detector, wherein the X-ray imaging apparatus further comprises a display unit for displaying the X-ray image, and wherein the controller is configured to notify that the direction of tilting the table top and the movement-prohibited direction coincide by displaying in the display unit that the direction of tilting the table top and the movement-prohibited direction coincide.

The invention claimed is:

1. An X-ray imaging apparatus comprising:

an X-ray irradiation unit configured to emit X-rays;

an X-ray detector configured to detect X-rays emitted from the X-ray irradiation unit;

a table top configured to place a subject thereon;

a table top driving mechanism configured to change a tilt of the table top;

an imaging unit configured to image the subject placed on the table top and a subject holding member provided on the table top to hold a posture of the subject;

an image processing unit configured to acquire presence or absence of the subject holding member, based on an image of the subject and the subject holding member captured by the imaging unit; and a controller, wherein the controller is configured to acquire a movement-prohibited direction which is a direction in which the subject holding member is not provided, based on the presence or absence of the subject holding member acquired by the image processing unit, determine whether a direction of tilting the table top by the table top driving mechanism and the movement-prohibited direction coincide, and perform, when the direction of tilting the table top and the movement-prohibited direction coincide, at least one of restricting an operation of the table top driving mechanism and notifying that the direction of tilting the table top and the movement-prohibited direction coincide.

2. The X-ray imaging apparatus as recited in claim 1, wherein when the direction of tilting the table top and the movement-prohibited direction coincide, the controller is configured to restrict the operation of the table top by the table top driving mechanism and to notify that the direction of tilting the table top and the movement-prohibited direction coincide.

3. The X-ray imaging apparatus as recited in claim 2, wherein the subject holding member includes at least one of a shoulder rest, a grip bar, and a stepping platform, wherein the image processing unit is configured to acquire the presence or absence of the subject holding member by acquiring whether at least one of the shoulder rest, the grip bar, and the stepping platform is provided on the table top, and wherein the controller is configured to determine whether the subject holding member corresponding to one of the shoulder rest, the grip bar, and the stepping platform is provided at a position corresponding to the direction of tilting the table top, and set a direction in which the subject holding member corresponding to one of the shoulder rest, the grip bar, and the stepping platform is not provided at a position corresponding to the direction of tiling the table top, as the movement-prohibited direction.

4. The X-ray imaging apparatus as recited in claim 3, wherein the image processing unit is configured to acquire the presence or absence of the subject holding member, an orientation of the subject on the table top, and the position of the subject holding member, based on the image of the subject and the subject holding member captured by the imaging unit, and wherein the controller is configured to set the movement-prohibited direction based on the orientation of the subject on the table top, the presence or absence of the subject holding member, and the position of the subject holding member.

5. The X-ray imaging apparatus as recited in claim 4, wherein the controller is configured to restrict the operation of the table top by the table top driving mechanism by prohibiting the operation of tilting the table top by the table top driving mechanism or by reducing a rate of tilting the table top by the table top driving mechanism.

6. The X-ray imaging apparatus as recited in claim 5, wherein the controller is configured to restrict the operation of tilting the table top by the table top driving mechanism by prohibiting the operation of tilting the table top by the table top driving mechanism, and continue prohibiting the operation of tilting the table top by the table top driving mechanism until receiving an operation input to release restricting the operation of the table top by the operator after prohibiting the operation of tilting the table top.

7. The X-ray imaging apparatus as recited in claim 6, wherein in a case in which the direction of tilting the table top coincides with the movement-prohibited direction, the controller is configured to restrict the operation of the table top by the table top driving mechanism after receiving an operation input to the table top driving mechanism to move the table top, and notify that the direction of tilting the table top and the movement-prohibited direction coincide.

8. The X-ray imaging apparatus as recited in claim 7, wherein the image processing unit is configured to acquire the position of the subject holding member by a trained model that has been trained to acquire the position of the subject holding member on the table top.

9. The X-ray imaging apparatus as recited in claim 1, further comprising:

a storage unit configured to store a relation between a type of the subject holding member and the direction of tilting the table top, wherein the controller is configured to store the relation between the type of the subject holding member and the direction of tilting the table top in the storage unit, based on an operation input of an operator, and allow the operation of the table top in the movement-prohibited direction when the movement in the movement-prohibited direction is permitted in the relation between the type of the subject holding member and the direction of tilting the table top stored in the storage unit, even when the direction of tilting the table top and the movement-prohibited direction coincide.

10. The X-ray imaging apparatus as recited in claim 1, wherein the imaging unit is provided at a position facing the table top in the housing of the X-ray irradiation unit.

11. The X-ray imaging apparatus as recited in claim 1, wherein the image processing unit is configured to generate an X-ray image based on X-rays detected by the X-ray detector, wherein the X-ray imaging apparatus further comprises a display unit for displaying the X-ray image, and wherein the controller is configured to notify that the direction of tilting the table top and the movement-prohibited direction coincide by displaying in the display unit that the direction of tilting the table top and the movement-prohibited direction coincide.

12. An X-ray imaging system comprising:

an X-ray irradiation unit configured to emit X-rays;

an X-ray detector configured to detect X-rays emitted from the X-ray irradiation unit;

a table top configured to place a subject thereon;

a table top driving mechanism configured to change a tilt of the table top;

an imaging unit configured to image the subject placed on the table top and a subject holding member provided on the table top to hold a posture of the subject;

an image processing unit configured to acquire presence or absence of the subject holding member, based on an image of the subject and the subject holding member captured by the imaging unit; and a controller, wherein the controller is configured to acquire a movement-prohibited direction which is a direction in which the subject holding member is not provided, based on the presence or absence of the subject holding member acquired by the image processing unit, determine whether a direction of tilting the table top by the table top driving mechanism and the movement-prohibited direction coincide, and perform, when the direction of tilting the table top and the movement-prohibited direction coincide, at least one of restricting an operation of the table top driving mechanism and notifying that the direction of tilting the table top and the movement-prohibited direction coincide.

13. The X-ray imaging system as recited in claim 12, wherein the image processing unit is configured to generate an X-ray image based on X-rays detected by the X-ray detector, wherein the X-ray imaging apparatus further comprises a display unit for displaying the X-ray image, and wherein the controller is configured to notify that the direction of tilting the table top and the movement-prohibited direction coincide by displaying in the display unit that the direction of tilting the table top and the movement-prohibited direction coincide.

* * * * *